(12) United States Patent
Lunak et al.

(10) Patent No.: US 8,571,701 B2
(45) Date of Patent: Oct. 29, 2013

(54) METHOD OF FILLING A RESTOCKING PACKAGE

(75) Inventors: Richard Lunak, Pittsburgh, PA (US); Payal Lal, Pittsburgh, PA (US); Gregory Hart, Sarver, PA (US); Manoj Wangu, Wexford, PA (US)

(73) Assignee: McKesson Automation Inc., Cranberry, PA (US)

( * ) Notice: Subject to any disclaimer, the term of this patent is extended or adjusted under 35 U.S.C. 154(b) by 1171 days.

(21) Appl. No.: 11/423,060

(22) Filed: Jun. 8, 2006

(65) Prior Publication Data

US 2007/0027577 A1 Feb. 1, 2007

Related U.S. Application Data

(60) Continuation of application No. 10/820,214, filed on Apr. 7, 2004, now Pat. No. 7,072,737, which is a division of application No. 09/998,488, filed on Nov. 30, 2001, now Pat. No. 6,847,861.

(51) Int. Cl.
*G06F 7/00* (2006.01)

(52) U.S. Cl.
USPC .......................................................... 700/216

(58) Field of Classification Search
USPC .................. 700/226, 241, 216, 244, 236, 242
See application file for complete search history.

(56) References Cited

U.S. PATENT DOCUMENTS

| | | |
|---|---|---|
| 2,964,370 A | 12/1960 | Butler |
| 3,556,342 A | 1/1971 | Guarr |
| 3,593,881 A | 7/1971 | Paap |
| 3,599,152 A | 8/1971 | Williams |
| 3,606,959 A | 9/1971 | Stonor |
| 3,675,816 A | 7/1972 | Bourke, II et al. |
| 3,732,544 A | 5/1973 | Obland |
| 3,744,867 A | 7/1973 | Shaw |
| 3,762,601 A | 10/1973 | McLaughlin |
| 3,858,181 A | 12/1974 | Goldsby et al. |
| 3,875,982 A | 4/1975 | Mizu et al. |
| 3,878,967 A | 4/1975 | Joslin et al. |
| 3,917,045 A | 11/1975 | Williams et al. |
| 3,948,454 A | 4/1976 | Bastian |

(Continued)

FOREIGN PATENT DOCUMENTS

| | | |
|---|---|---|
| CA | 936501 | 11/1973 |
| CA | 2412801 | 5/2003 |

(Continued)

OTHER PUBLICATIONS

McKesson Automation, Admin-Rx TM, article from website: http://www.mckessonautomation.com/wt/auto/tech_fornursing_admin, Feb. 24, 2005, pp. 1-2.

(Continued)

*Primary Examiner* — Ramya Burgess
(74) *Attorney, Agent, or Firm* — Alston & Bird LLP

(57) ABSTRACT

A method of filling a restocking package is provided in which a queue of requests of items to be picked from a carousel is evaluated based on a set of user configurable priorities, a carousel is operated based on said evaluating, items are picked from the carousel in response to said operating, and a restocking package is filled with items held in said carousel in response to said operating. The method may additionally comprise filling the restocking package at a configurable time.

20 Claims, 19 Drawing Sheets

(56) References Cited

U.S. PATENT DOCUMENTS

| | | | |
|---|---|---|---|
| 3,998,356 A | 12/1976 | Christensen | |
| 4,020,972 A | 5/1977 | Lundblad | |
| 4,135,241 A | 1/1979 | Stanis et al. | |
| 4,225,930 A | 9/1980 | Steffen | |
| 4,237,536 A | 12/1980 | Enelow et al. | |
| 4,267,942 A | 5/1981 | Wick, Jr. et al. | |
| 4,293,845 A | 10/1981 | Villa-Real | |
| 4,342,404 A | 8/1982 | Baker | |
| 4,360,125 A | 11/1982 | Martindale et al. | |
| 4,412,292 A | 10/1983 | Sedam et al. | |
| 4,473,884 A | 9/1984 | Behl | |
| 4,504,153 A | 3/1985 | Schollmeyer et al. | |
| 4,546,901 A | 10/1985 | Buttarazzi | |
| 4,616,316 A | 10/1986 | Hanpeter et al. | |
| 4,655,026 A | 4/1987 | Wigoda | |
| 4,664,289 A | 5/1987 | Shimizu et al. | |
| 4,695,954 A | 9/1987 | Rose et al. | |
| 4,717,042 A | 1/1988 | McLaughlin | |
| 4,725,997 A | 2/1988 | Urquhart et al. | |
| 4,733,362 A | 3/1988 | Haraguchi | |
| 4,737,910 A | 4/1988 | Kimbrow | |
| 4,766,542 A | 8/1988 | Pilarczyk | |
| 4,766,548 A | 8/1988 | Cedrone et al. | |
| 4,779,938 A | 10/1988 | Johnston | |
| 4,785,969 A | 11/1988 | McLaughlin | |
| 4,811,764 A | 3/1989 | McLaughlin | |
| 4,812,629 A | 3/1989 | O'Neil et al. | |
| 4,813,752 A | 3/1989 | Schindler | |
| 4,813,753 A | 3/1989 | Relyea | |
| 4,831,562 A | 5/1989 | McIntosh et al. | |
| 4,839,806 A | 6/1989 | Goldfischer et al. | |
| 4,847,764 A | 7/1989 | Halvorson | |
| 4,857,713 A | 8/1989 | Brown | |
| 4,953,745 A | 9/1990 | Rowlett, Jr. | |
| 4,967,928 A | 11/1990 | Carter | |
| 5,014,875 A | 5/1991 | McLaughlin et al. | |
| 5,047,948 A | 9/1991 | Turner | |
| 5,171,120 A | 12/1992 | Bernard, II et al. | |
| 5,190,185 A | 3/1993 | Blechl | |
| 5,205,436 A | 4/1993 | Savage | |
| 5,246,332 A | 9/1993 | Bernard, II et al. | |
| 5,272,321 A | 12/1993 | Otsuka et al. | |
| 5,314,243 A | 5/1994 | McDonald et al. | |
| 5,346,297 A | 9/1994 | Colson, Jr. et al. | |
| 5,363,310 A | 11/1994 | Haj-Ali-Ahmadi et al. | |
| 5,377,864 A | 1/1995 | Blechl et al. | |
| 5,405,048 A | 4/1995 | Rogers et al. | |
| 5,408,443 A | 4/1995 | Weinberger | |
| 5,431,299 A | 7/1995 | Brewer et al. | |
| 5,438,523 A | 8/1995 | Humm et al. | |
| 5,460,294 A | 10/1995 | Williams | |
| 5,468,110 A | 11/1995 | McDonald et al. | |
| 5,472,309 A | 12/1995 | Bernard, II et al. | |
| 5,480,062 A | 1/1996 | Rogers et al. | |
| 5,484,991 A | 1/1996 | Sherman et al. | |
| 5,502,944 A | 4/1996 | Kraft et al. | |
| 5,520,450 A | 5/1996 | Colson, Jr. et al. | |
| 5,564,803 A | 10/1996 | McDonald et al. | |
| 5,585,473 A | 12/1996 | Bendiak | |
| 5,593,267 A | 1/1997 | McDonald et al. | |
| 5,597,995 A | 1/1997 | Williams et al. | |
| 5,608,643 A | 3/1997 | Wichter et al. | |
| 5,611,051 A * | 3/1997 | Pirelli | 705/7.31 |
| 5,661,978 A | 9/1997 | Holmes et al. | |
| D384,578 S | 10/1997 | Wangu et al. | |
| 5,713,485 A * | 2/1998 | Liff et al. | 221/2 |
| 5,716,114 A | 2/1998 | Holmes et al. | |
| 5,722,332 A | 3/1998 | Fumanelli | |
| 5,745,366 A | 4/1998 | Higham et al. | |
| 5,761,877 A | 6/1998 | Quandt | |
| 5,781,442 A | 7/1998 | Engleson et al. | |
| 5,790,409 A | 8/1998 | Fedor et al. | |
| 5,797,515 A | 8/1998 | Liff et al. | |
| 5,805,455 A | 9/1998 | Lipps | |
| 5,805,456 A | 9/1998 | Higham et al. | |
| 5,808,289 A | 9/1998 | Becker | |
| 5,820,237 A | 10/1998 | Robey | |
| 5,842,976 A | 12/1998 | Williamson | |
| 5,877,962 A | 3/1999 | Radcliffe | |
| 5,878,885 A | 3/1999 | Wangu et al. | |
| 5,880,443 A | 3/1999 | McDonald et al. | |
| 5,883,806 A * | 3/1999 | Meador et al. | 700/244 |
| 5,893,697 A | 4/1999 | Zini et al. | |
| 5,905,653 A | 5/1999 | Higham et al. | |
| 5,907,493 A | 5/1999 | Boyer et al. | |
| 5,912,818 A | 6/1999 | McGrady et al. | |
| 5,927,540 A | 7/1999 | Godlewski | |
| 5,940,306 A | 8/1999 | Gardner et al. | |
| 5,957,372 A | 9/1999 | Dean et al. | |
| 5,971,593 A | 10/1999 | McGrady | |
| 5,993,046 A | 11/1999 | McGrady et al. | |
| 6,003,006 A | 12/1999 | Colella et al. | |
| 6,011,999 A | 1/2000 | Holmes | |
| 6,019,249 A | 2/2000 | Michael et al. | |
| 6,021,392 A | 2/2000 | Lester et al. | |
| 6,027,019 A | 2/2000 | Kou | |
| 6,039,467 A | 3/2000 | Holmes | |
| 6,065,819 A | 5/2000 | Holmes et al. | |
| 6,068,156 A | 5/2000 | Liff et al. | |
| 6,073,834 A | 6/2000 | Michael et al. | |
| 6,108,588 A | 8/2000 | McGrady | |
| 6,109,774 A | 8/2000 | Holmes et al. | |
| 6,112,502 A | 9/2000 | Frederick et al. | |
| 6,116,461 A | 9/2000 | Broadfield et al. | |
| 6,151,536 A | 11/2000 | Arnold et al. | |
| 6,170,230 B1 | 1/2001 | Chudy et al. | |
| 6,170,929 B1 | 1/2001 | Wilson et al. | |
| 6,175,779 B1 | 1/2001 | Barrett | |
| 6,176,392 B1 | 1/2001 | William et al. | |
| 6,181,982 B1 | 1/2001 | Yuyama et al. | |
| 6,189,727 B1 | 2/2001 | Shoenfeld | |
| 6,189,788 B1 | 2/2001 | Sherman et al. | |
| 6,223,934 B1 | 5/2001 | Shoenfeld | |
| 6,256,967 B1 | 7/2001 | Hebron et al. | |
| 6,283,322 B1 | 9/2001 | Liff et al. | |
| 6,289,656 B1 | 9/2001 | Wangu et al. | |
| 6,317,648 B1 | 11/2001 | Sleep et al. | |
| 6,332,100 B1 | 12/2001 | Sahai et al. | |
| 6,338,007 B1 | 1/2002 | Broadfield et al. | |
| 6,339,732 B1 | 1/2002 | Phoon et al. | |
| 6,354,783 B1 | 3/2002 | Stoy et al. | |
| 6,361,263 B1 | 3/2002 | Dewey et al. | |
| 6,364,517 B1 | 4/2002 | Yuyama et al. | |
| 6,370,841 B1 | 4/2002 | Chudy et al. | |
| 6,385,505 B1 | 5/2002 | Lipps | |
| 6,393,339 B1 | 5/2002 | Yeadon | |
| 6,418,416 B1 | 7/2002 | Rosenberg et al. | |
| RE37,829 E | 9/2002 | Charhut et al. | |
| 6,449,927 B2 | 9/2002 | Hebron et al. | |
| 6,470,234 B1 | 10/2002 | McGrady | |
| 6,471,089 B2 | 10/2002 | Liff et al. | |
| 6,490,502 B2 * | 12/2002 | Fellows et al. | 700/231 |
| 6,497,342 B2 | 12/2002 | Zhang et al. | |
| 6,499,270 B2 * | 12/2002 | Peroni et al. | 53/53 |
| 6,529,801 B1 | 3/2003 | Rosenblum | |
| 6,530,517 B1 | 3/2003 | Kou | |
| 6,532,399 B2 | 3/2003 | Mase | |
| 6,564,121 B1 | 5/2003 | Wallace et al. | |
| 6,581,798 B2 | 6/2003 | Liff et al. | |
| 6,604,019 B2 | 8/2003 | Ahlin et al. | |
| 6,609,047 B1 | 8/2003 | Lipps | |
| 6,611,733 B1 | 8/2003 | De La Huerga | |
| 6,625,952 B1 | 9/2003 | Chudy et al. | |
| 6,636,780 B1 | 10/2003 | Haitin et al. | |
| 6,640,159 B2 | 10/2003 | Holmes et al. | |
| 6,650,964 B2 | 11/2003 | Spano, Jr. et al. | |
| 6,671,579 B2 | 12/2003 | Spano, Jr. et al. | |
| 6,681,149 B2 | 1/2004 | William et al. | |
| 6,733,095 B1 | 5/2004 | Rieb | |
| 6,735,497 B2 | 5/2004 | Wallace et al. | |
| 6,742,671 B2 | 6/2004 | Hebron et al. | |
| 6,755,931 B2 | 6/2004 | Vollm et al. | |
| 6,760,643 B2 | 7/2004 | Lipps | |
| 6,775,591 B1 | 8/2004 | Shoenfeld | |

(56) References Cited

U.S. PATENT DOCUMENTS

| | | |
|---|---|---|
| 6,776,304 B2 | 8/2004 | Liff et al. |
| 6,785,589 B2 | 8/2004 | Eggenberger et al. |
| 6,788,997 B1 | 9/2004 | Frederick |
| 6,790,198 B1 | 9/2004 | White et al. |
| 6,811,088 B2 | 11/2004 | Lanzaro et al. |
| 6,814,254 B2 | 11/2004 | Liff et al. |
| 6,814,255 B2 | 11/2004 | Liff et al. |
| 6,823,084 B2 | 11/2004 | Myers et al. |
| 6,847,861 B2 | 1/2005 | Lunak et al. |
| 6,874,684 B1 | 4/2005 | Denenberg et al. |
| 6,892,780 B2 | 5/2005 | Vollm et al. |
| 6,895,304 B2 | 5/2005 | Spano, Jr. et al. |
| 6,935,560 B2 | 8/2005 | Andreasson et al. |
| 6,975,922 B2 | 12/2005 | Duncan et al. |
| 6,985,797 B2 | 1/2006 | Spano, Jr. et al. |
| 6,996,455 B2 | 2/2006 | Eggenberger et al. |
| 7,010,389 B2 | 3/2006 | Lunak et al. |
| 7,014,063 B2 | 3/2006 | Shows et al. |
| 7,016,766 B2 | 3/2006 | William et al. |
| 7,040,504 B2 | 5/2006 | Broadfield et al. |
| 7,052,097 B2 | 5/2006 | Meek, Jr. et al. |
| 7,072,737 B2 | 7/2006 | Lunak et al. |
| 7,072,855 B1 | 7/2006 | Godlewski et al. |
| 7,077,286 B2 | 7/2006 | Shows et al. |
| 7,085,621 B2 | 8/2006 | Spano, Jr. et al. |
| 7,092,796 B2 | 8/2006 | Vanderveen |
| 7,093,755 B2 | 8/2006 | Jordan et al. |
| 7,100,792 B2 | 9/2006 | Hunter et al. |
| 7,103,419 B2 | 9/2006 | Engleson et al. |
| 7,111,780 B2 | 9/2006 | Broussard et al. |
| 7,139,639 B2 | 11/2006 | Broussard et al. |
| 7,150,724 B2 | 12/2006 | Morris et al. |
| 7,155,306 B2 | 12/2006 | Haitin et al. |
| 7,171,277 B2 | 1/2007 | Engleson et al. |
| 7,218,231 B2 | 5/2007 | Higham |
| 7,228,198 B2 | 6/2007 | Vollm et al. |
| 7,249,688 B2 | 7/2007 | Hunter et al. |
| 7,260,402 B1 | 8/2007 | Ahmed |
| 7,348,884 B2 | 3/2008 | Higham |
| 7,417,729 B2 | 8/2008 | Greenwald |
| 7,419,133 B2 | 9/2008 | Clarke et al. |
| 7,426,425 B2 | 9/2008 | Meek, Jr. et al. |
| 7,554,449 B2 | 6/2009 | Higham |
| 7,568,627 B2 | 8/2009 | Lunak et al. |
| 7,571,024 B2 | 8/2009 | Duncan et al. |
| 7,588,167 B2 | 9/2009 | Hunter et al. |
| 2001/0032035 A1 | 10/2001 | Holmes et al. |
| 2002/0032582 A1 | 3/2002 | Feeney, Jr. et al. |
| 2002/0091593 A1 | 7/2002 | Fowler |
| 2002/0147597 A1 | 10/2002 | Connors et al. |
| 2003/0060926 A1* | 3/2003 | Yuyama et al. ............... 700/237 |
| 2003/0105555 A1 | 6/2003 | Lunak et al. |
| 2003/0117281 A1 | 6/2003 | Sriharto et al. |
| 2003/0120384 A1 | 6/2003 | Haitin et al. |
| 2003/0144882 A1 | 7/2003 | Talachian et al. |
| 2004/0054436 A1 | 3/2004 | Haitin et al. |
| 2004/0104652 A1 | 6/2004 | Holmes et al. |
| 2004/0225527 A1 | 11/2004 | Holz |
| 2004/0225528 A1 | 11/2004 | Brock |
| 2005/0096785 A1 | 5/2005 | Moncrief et al. |
| 2005/0113970 A1 | 5/2005 | Holmes et al. |
| 2005/0149379 A1 | 7/2005 | Cyr et al. |
| 2005/0216310 A1 | 9/2005 | Clements et al. |
| 2006/0079994 A1 | 4/2006 | Chu et al. |
| 2006/0190297 A1 | 8/2006 | Glass et al. |

FOREIGN PATENT DOCUMENTS

| | | |
|---|---|---|
| DE | 3040580 | 5/1982 |
| DE | 3205620 | 9/1982 |
| EP | 0037649 A2 | 10/1981 |
| EP | 0208029 A1 | 1/1987 |
| EP | 0249367 A2 | 12/1987 |
| JP | 77051755 | 12/1978 |
| JP | 78058513 | 11/1979 |
| JP | 83076764 | 5/1983 |
| JP | 84056958 | 4/1984 |
| JP | 8345388 | 10/1984 |
| JP | 85069771 | 10/1986 |
| JP | 85112661 | 12/1986 |
| WO | WO 86/06048 | 10/1986 |
| WO | WO-03/071943 A2 | 9/2003 |
| WO | WO 2006/078737 A2 | 7/2006 |

OTHER PUBLICATIONS

McKesson Automation, AcuDose-Rx TM, article from website: http://www.Mckessonautomation.com/wt/auto/techforpharmacy_acudoserx, Feb. 24, 2005, pp. 1-2.

International Search Report for Application No. PCT/US2004/039527 dated Oct. 10, 2005.

International Preliminary Report on Patentability and Written Opinion for Application No. PCT/US2004/039527 May 29, 2006.

Office Action for Canadian Application No. 2,451,069 dated Jan. 5, 2007.

Notice of Allowance for Canadian Application No. 2,451,069 dated Aug. 1, 2008.

Office Action for Canadian Application No. 2,547,246 dated Feb. 12, 2009.

Office Action for Canadian Application No. 2,547,246 dated Feb. 22, 2010.

Office Action for Canadian Application No. 2,635,881 dated Jul. 6, 2011.

Office Action for Canadian Application No. 2,635,881 dated May 30, 2012.

Non-Final Office Action for U.S. Appl. No. 10/820,209 dated Oct. 5, 2004.

Final Office Action for U.S. Appl. No. 10/820,209 dated Mar. 8, 2005.

Non-Final Office Action for U.S. Appl. No. 10/820,209 dated Aug. 11, 2005.

Final Office Action for U.S. Appl. No. 10/820,209 dated Jan. 24, 2006.

Advisory Action for U.S. Appl. No. 10/820,209 dated May 10, 2006.

Non-Final Office Action for U.S. Appl. No. 10/820,209 dated Sep. 7, 2006.

Non-Final Office Action for U.S. Appl. No. 10/820,209 dated Mar. 12, 2007.

Interview Summary for U.S. Appl. No. 10/820,209 dated May 1, 2007.

Non-Final Office Action for U.S. Appl. No. 10/820,209 dated Jan. 14, 2009.

Non-Final Office Action for U.S. Appl. No. 10/820,209 dated Aug. 27, 2009.

Final Office Action for U.S. Appl. No. 10/820,209 dated Feb. 26, 2010.

Notice of Allowance for U.S. Appl. No. 10/820,209 dated May 14, 2010.

Non-Final Office Action for U.S. Appl. No. 10/820,214 dated Mar. 22, 2005.

Final Office Action for U.S. Appl. No. 10/820,214 dated Aug. 3, 2005.

Notice of Allowance for U.S. Appl. No. 10/820,214 dated Feb. 14, 2006.

Supplemental Notice of Allowance for U.S. Appl. No. 10/820,214 dated Mar. 2, 2006.

Non-Final Office Action for U.S. Appl. No. 10/820,208 dated Sep. 30, 2004.

Final Office Action for U.S. Appl. No. 10/820,208 dated Jan. 26, 2005.

Notice of Allowance for U.S. Appl. No. 10/820,208 dated Jul. 29, 2005.

Non-Final Office Action for U.S. Appl. No. 10/820,213 dated Mar. 10, 2006.

Advisory Action for U.S. Appl. No. 10/820,213 dated Mar. 29, 2007.

Final Office Action for U.S. Appl. No. 10/820,213 dated Nov. 27, 2006.

(56) References Cited

OTHER PUBLICATIONS

Non-Final Office Action for U.S. Appl. No. 10/820,213 dated Dec. 11, 2007.
Final Office Action for U.S. Appl. No. 10/820,213 dated May 9, 2008.
Notice of Allowance for U.S. Appl. No. 10/820,213 dated Mar. 30, 2009.
Non-Final Office Action for U.S. Appl. No. 09/998,488 dated Jun. 12, 2003.
Final Office Action for U.S. Appl. No. 09/998,488 dated Nov. 13, 2003.
Notice of Allowance for U.S. Appl. No. 09/998,488 dated Mar. 15, 2004.
Office Action for U.S. Appl. No. 10/313,554 dated Dec. 22, 2004.
Office Action for U.S. Appl. No. 10/313,554 dated Jun. 28, 2005.
Office Action for U.S. Appl. No. 10/313,554 dated Aug. 26, 2005.
Notice of Allowability for U.S. Appl. No. 10/313,554 dated Oct. 17, 2005.
Office Action for U.S. Appl. No. 10/996,835 dated Dec. 26, 2006.
Final Office Action for U.S. Appl. No. 10/996,835 dated Apr. 18, 2007.
Office Action for U.S. Appl. No. 10/996,835 dated Sep. 27, 2007.
Final Office Action for U.S. Appl. No. 10/996,835 dated Mar. 17, 2008.
Notice of Panel Decision from Pre-Appeal Brief Review (Reopen Prosecution) for U.S. Appl. No. 10/996,835 dated Jul. 17, 2008.
Office Action for U.S. Appl. No. 10/996,835 dated Sep. 18, 2008.
Final Office Action for U.S. Appl. No. 10/996,835 dated Feb. 25, 2009.
Final Office Action for U.S. Appl. No. 10/996,835 dated Jun. 16, 2009.
Office Action for U.S. Appl. No. 10/996,835 dated Jan. 8, 2010.
Notice of Allowance for U.S. Appl. No. 10/996,835 dated Jun. 25, 2010.
Supplemental Notice of Allowance for U.S. Appl. No. 10/996,835 dated Sep. 1, 2010.
Office Action for U.S. Appl. No. 11/369,779 dated Dec. 6, 2006.
Office Action for U.S. Appl. No. 11/369,779 Jun. 4, 2007.
Office Action for U.S. Appl. No. 11/369,779 Oct. 30, 2007.
Notice of Allowance for U.S. Appl. No. 11/369,779 dated May 12, 2008.
Office Action for U.S. Appl. No. 11/369,780 dated May 20, 2008.
Office Action for U.S. Appl. No. 11/369,780 dated Nov. 13, 2008.
Office Action for U.S. Appl. No. 11/369,780 dated Apr. 29, 2009.
Advisory Action for U.S. Appl. No. 11/369,780 Mar. 5, 2009.
Office Action for U.S. Appl. No. 11/369,780 dated Nov. 3, 2009.
Office Action for U.S. Appl. No. 11/369,780 dated Aug. 3, 2010.
Final Office Action for U.S. Appl. No. 11/369,780 dated Jan. 14, 2011.
Final Office Action for U.S. Appl. No. 11/369,780 dated Aug. 9, 2011.
Office Action for U.S. Appl. No. 12/194,105 dated Feb. 25, 2009.
Office Action for U.S. Appl. No. 12/194,105 dated Sep. 2, 2009.
Interview Summary for U.S. Appl. No. 12/194,105 dated Dec. 8, 2009.
Office Action for U.S. Appl. No. 12/194,105 dated Mar. 29, 2010.
Office Action for U.S. Appl. No. 12/194,105 dated Aug. 26, 2010.
Notice of Allowance for U.S. Appl. No. 12/194,105 dated Dec. 9, 2010.
Supplemental Notice of Allowance for U.S. Appl. No. 12/194,105 dated Mar. 7, 2011.
Office Action for U.S. Appl. No. 11/756,486 dated Jun. 28, 2010.
Final Office Action for U.S. Appl. No. 11/756,486 dated Oct. 26, 2010.
Weissman et al. (1978) Med. Instrumentation 12(4):237-240.
Simon et al. (1976) Am. J. Hosp. Pharm. 33:459-463.
Encyclopedia of Computer Science and Engineering $2^{nd}$ Ed. (1983) Ralston & Reilly, Jr. Eds. Van Nostrand Reinhold Co., NY pp. 686-688, 939-941.
J.A. Dickerson et al. (1975) IBM Technical Disclosure Bulletin 18(6):1967-1972.
J.H. Hull et al. (1974) J. Clinical Computing 3(4):295-309.
K.N. Baker et al. (1963) Am. J. Hosp. Pharm. 20(11):568-579.
B.J. Means et al. (1975) Am. J. Hosp. Pharm. 32:186-191.
W.L. Gousse (1978) Am. J. Hosp. Pharm. 35:711-714.
D.M. Colaluca et al. (1983) Am. J. Hosp. Pharm. 18:68-69, 74-76.
H.J. Derewicz et al. (1973) Am. J. Hosp. Pharm. 30:206-212.
K.W. Burleson (1982) Am. J. Hosp. Pharm. 39:53-70.
D.S. Swanson et al. (1982) Am. J. Hosp. Pharm. 39:2109-2117.
G.C. Unertl (1984) Am. J. Hosp. Pharm. 41:1131-1136.
G. Gilroy et al. (1977) Am. J. Hosp. Pharm. 34(2):155-162 Abstract.
C.G. Schroeder et al. (1986) Am. J. Hosp. Pharm. 43:355-359 Abstract.
S.N. Cohen et al. "A computer-based system for prospective identification of drug interactions" (1972) pp. 228-end.
V.F. Sytnik "Control of spare part stores by computer" (1972) INSPEC Abstract No. C72016808.
P.J. LeBeux "Frame selection systems and languages for medical applications" (1974) INSPEC Abstract No. C75011713.
A. Kemp-Davies "Dispense with the drudgery (computerizing pharmacies)" (1987) INSPEC Abstract No. C87024679, D87001123.
H. Ishizuka et al. "Computerized prescription checking system" Int. J. Bio-Medical Computing 19 (1986) pp. 195-200.
Y. Kishida et al. "Ordering system's tool in hospital information systems use" NEC Research & Development, No. 84, (1987), pp. 120-123.
I. Matwshyn et al. "Reducing materials management costs with microcomputers" (1984) Healthcare Financial Management, pp. 58-62.
Computer Applications in Medical Care, IEEE Computer Society Proceedings, Nov. 4-7, 1984, pp. 246-250.
J.B. Ennis "Hospital information systems—data abase approach" (1983) AAMSI Congress 83, pp. 22-24.
P.A.M. Griep et al. "Office automation and further. X. The design of an architecture for coupling different information systems. A method developed in the health service". (1987) INSPEC Abstract No. C87042382.
M. Hayman "Controlling the supply of drugs" (1985) vol. 27, No. 3, Apr. 1985, Data Pro pp. 25.
T.W. Kohout et al. (1983) Am. J. Hosp. Pharm. 40:606-608 Abstract.
J.L. Hamm et al. (1984) Am. J. Hosp. Pharm. 41(7):1358-1360 Abstract.
T.D. Moore et al. (1984) Am. J. Hosp. Pharm. 41(11) 2384-2389 Abstract.
R.L. Moss et al. (1985) Am. J. Hosp. Pharm. 42:309-312 Abstract.
T.L. Dotson (1986) Am. J. Hosp. Pharm. 43(3):658-663 Abstract.
M.J. Haumschild et al. (1987) Am. J. Hosp. Pharm. 44(2):345-348 Abstract.
The Baker Vertical Carousel Advertisement "Bulk pharmacy storage is looking up!" Baker APS, Pneville, LA, two pages.
Baker Carousel-white carousel operation instructions, 2000 Series Power File, 16 pages.
Pharmacy 2000 User's Guide, Oct. 9, 2003, pp. i-v, Chapters 1-14.
Japanese Medical Pharmacy (1987) 21(3):27-31.
Japanese Medical Pharmacy (1985) 19(6):21-24.
Japanese Institution (1980) 32(3):62-67, 164.

* cited by examiner

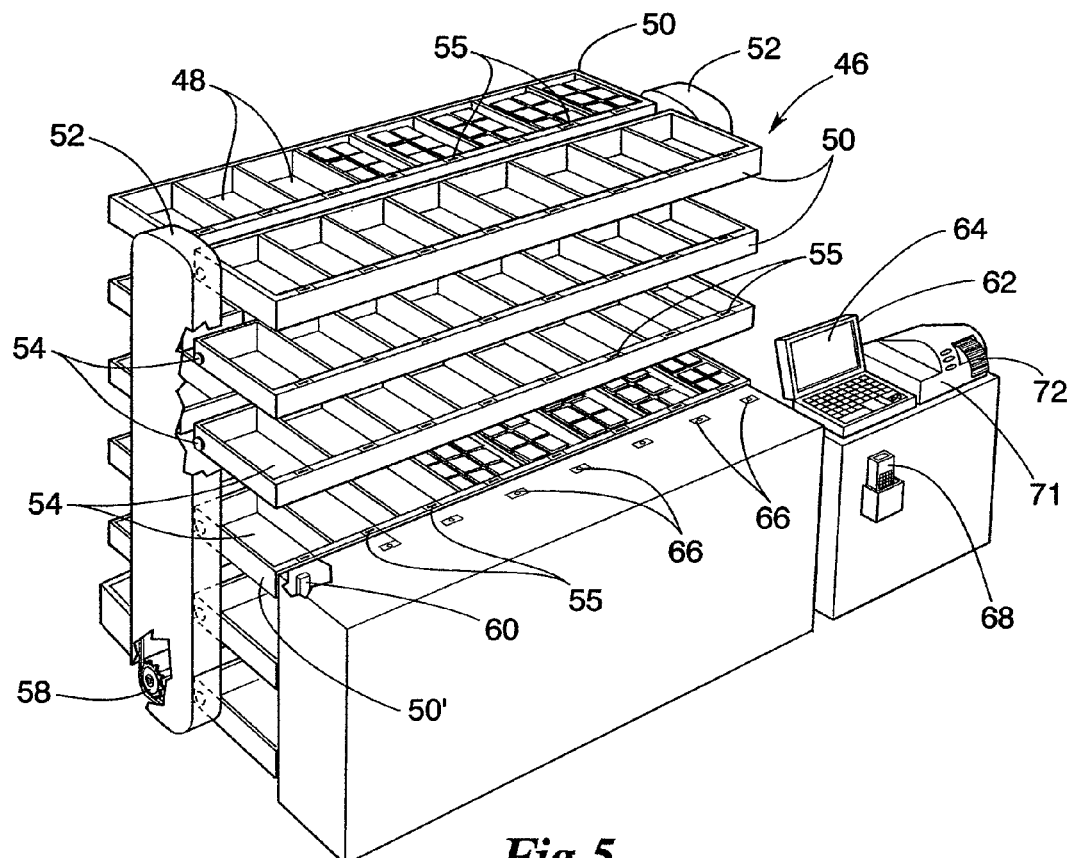
Fig.5
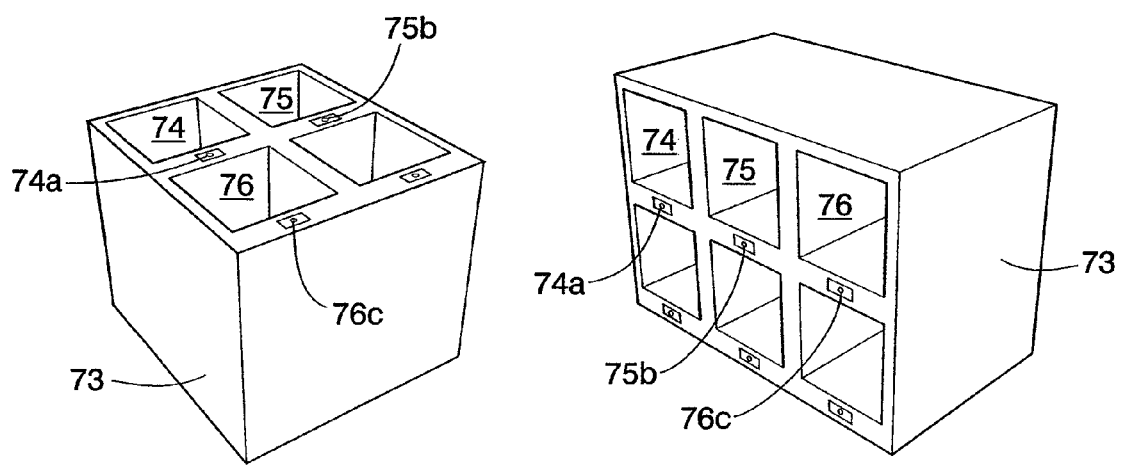
Fig.5a      Fig.5b

METHOD OF FILLING A RESTOCKING PACKAGE

CROSS-REFERENCE TO RELATED APPLICATIONS

This application is a continuation of U.S. application Ser. No. 10/820,214, filed Apr. 7, 2004 now U.S. Pat. No. 7,072,737, which application is a divisional of U.S. application Ser. No. 09/998,488 filed Nov. 30, 2001 now U.S. Pat. No. 6,847,861, all applications are hereby incorporated herein in their entireties by reference.

FIELD OF THE INVENTION

The present invention is directed generally to dispensing systems, and more particularly to methods of filling restocking packages within dispensing systems.

BACKGROUND OF THE INVENTION

Medical facilities, such as hospitals, nursing homes, etc., have a centralized location such as a pharmacy department or materials management department within the facility to coordinate the dispensing of drugs or medical supplies to the patients of the medical facility. The departments utilizing medications and medical supplies in such facilities have long been burdened with the increasingly complex record keeping and inventory management that results from caring for hundreds, if not thousands, of patients every day. Various methods have been employed to assist a centralized pharmacy or other centralized medical supply departments with maintaining accurate records while attempting to reduce the burden of managing all of the information associated with the distribution of medications and medical supplies. The responsibilities of the centralized supply include: filling individual patient prescriptions on a daily basis; administration of drugs using the five rights: right drug, right patient, right dose, right time and right route; dispensing medical supplies to patients; maintaining sufficient inventory of each drug or medical supply so as to have sufficient quantities on hand to administer to patients on a daily basis; tracking of drug interactions to prevent a patient from being given a drug that has adverse affects when combined with other drugs; accounting for the purchase of medications and medical supplies for use in the facility; accounting associated with dispensing of medications and medical supplies to individual patients; tracking of medication expiration dates to rid inventories of expired medications; and tracking of drug lot numbers, for example, in the event of a recall of a particular drug or drug lot number.

Medical facilities will dispense medications in one of three modes: centralized, decentralized, or a hybrid of partial decentralization. In facilities that are partly or fully decentralized, a very important function of the centralized pharmacy or materials management department is to restock various inventory locations, e.g. nurses stations, unit-based cabinets, satellite pharmacies, or off-site facilities in a network, with the quantity and types of medications and medical supplies that must be dispensed by the decentralized locations on a daily basis.

The need for storage locations in medical facilities remote from the centralized storage location stems from the need to be able to quickly and conveniently dispense medications and medical supplies (whether controlled or uncontrolled) to patients. To be able to dispense, there must be adequate supplies of the medications and medical supplies in the remote storage locations. To maintain the proper level of medications and medical supplies, accurate inventory control is necessary. Barring access to controlled substances by unauthorized personnel is also a necessary feature. The contents of these storage locations varies depending upon the medical procedures practiced in the area where the storage location is situated. For example, a storage location near an emergency room will be stocked differently than a storage location next to a surgical suite. Nevertheless, it is important to provide adequate supplies of all the required medications and medical supplies. It is also necessary to ensure that sufficient supplies are maintained at the decentralized and centralized storage locations without overstocking, because overstocking increases the cost of inventory by requiring more items to be maintained in inventory than are actually needed. Overstocking of inventory can also result in waste through spoilage of unused supplies. Excessive restocking of locations is also demanding on the facility's staff who must devote more of their time to monitor the storage locations to ensure that sufficient supplies are available.

A variety of systems have been developed to restock storage locations or to fill patient medication/supply orders. In one such system, referred to as a "cart exchange" system, dispensing carts distributed at dispensing locations in a medical facility are periodically exchanged with fully supplied carts. These carts contain medications which satisfy the patients' current medications orders. The "used" cart is returned to the central supply area where inventory decreases of particular medications or medical supplies are recorded and the cart is restocked to predetermined "par" levels. These par levels are intended to ensure constant availability of required medications or medical supplies.

In a similar system, individual carts are used but are not removed from their dispensing locations in the medical facility. Instead, a larger cart holding a variety of medications and medical supplies is circulated throughout the facility to restock individual carts to their par levels.

Although these systems are generally effective in restocking locations, they suffer from a number of drawbacks. One particular drawback is the potential for stock-outs that can arise if the inventories of the carts are not closely monitored. Adequate inventory monitoring can be problematic due to time limitations on the staff. Depletion of certain items from the carts can pose serious risks to the patients in the medical facility. Another drawback is that restocking storage locations is a very labor-intensive and inefficient process, especially when accurate inventory levels are not maintained in the centralized or decentralized location. Sites with decentralized locations usually have many different locations, each of which is individually restocked.

More recently, storage areas are being provided with dispensing carts or cabinets having computer processors for recording removal of medications or medical supplies from the dispensing cabinets. These carts or cabinets commonly include locked drawers having locked medication receptacles, and include computers. The computers commonly provide for limited access by selected medical personnel to such carts and cabinets and limited access to specific drawers or locations therein in response to entry of information into the computer. The computer creates inventory information for use by medical staff to ensure the continuity of the inventory in the carts or cabinets.

A system for restocking such computer controlled carts and cabinets is entitled Automated Restocking of Distributed Medication Dispensing Cabinets Using An Automated Medication Dispensing System, disclosed in U.S. application Ser. No. 09/480,819 and assigned to the same assignee as the present invention. The disclosed system automatically fills restock packages based on inventory information or configuration changes provided by various carts and cabinets located at the decentralized storage locations. The system encodes or otherwise disposes on the restock package an information carrier containing identifying information. To restock a dispensing cart or cabinet, a staff member decodes the information carrier encoded on the restock package. That may be accomplished by scanning a bar code or manually entering information into the cart's or cabinet's computer. Once the cart or cabinet confirms that the restock package is intended for it, the staff member loads the contents of the restock package into the cart or cabinet.

While the system of U.S. application Ser. No. 09/480,819 offers substantial advantages over other systems, some facilities may not have the resources to convert to such an automated system. Further, the facility may have the need to restock items which cannot be easily placed into a restocking package by automated equipment because of their size, weight, or configuration. Still other items may come from their manufacturers in bulk quantities or other types of packaging that make it difficult to automatically load them into a restocking package. Thus, the need exists for a restocking system that is at least in part manual, while taking advantage of the data generated by computer controlled carts and computer controlled cabinets. The need also exists for a restocking system that is at least in part manual, but can work side by side with computer automated restocking systems.

BRIEF SUMMARY OF THE INVENTION

A method of filling a restocking package is provided in which a queue of requests of items to be picked from a carousel is evaluated based on a set of user configurable priorities, a carousel is operated based on the evaluating, items are picked from the carousel in response to the operating, and a restocking package is filled with items held in the carousel in response to the operating. The method may additionally comprise filling the restocking package at a configurable time.

In an alternative embodiment, a method of filling a restocking package is provided in which an envelope is filled with items in a centralized storage location, the envelope is delivered to a dispensing device at a decentralized location and inserted into a lock-lidded, patient specific location in the dispensing device. The method may additionally comprise scanning a bar code on the envelope to identify a patient specific location for the envelope and for updating the dispensing device's records.

Inserting a lock-lidded, patient specific location in the dispensing device may include placing a tote containing patient specific envelopes into the dispensing device. The tote may contain a chip having information about the contents of the tote. As such, the method may additionally comprise dispensing from the tote, and modifying the information in the chip in response to the dispensing.

The centralized storage location may include an automation device. As such, the method may additionally comprise returning the tote to the centralized storage location, and connecting the tote to the automation device, enabling the automation device to access the information in the chip. The method may additionally comprise tracking delivery times of the envelopes.

In another alternative embodiment, a method of filling a restocking package is provided in which a restocking package is filled with items in a centralized storage location, a plurality of restocking packages are loaded into a cart, the cart containing the plurality of restocking packages is delivered to a dispensing device at a decentralized location, and the cart carrying the plurality of restocking packages is connected to the dispensing device. The restocking packages may include a plurality of patient specific envelopes.

The cart may contain a chip having information about the contents of the cart. As such, the method may additionally comprise dispensing from the cart, and modifying the information in the chip in response to the dispensing. The method may further comprise tracking delivery times of restocking packages.

BRIEF DESCRIPTION OF THE SEVERAL
VIEWS OF THE DRAWING(S)

Having thus described the invention in general terms, reference will now be made to the accompanying drawings, which are not necessarily drawn to scale, and wherein:

FIG. 5 is one example of hardware located at the central location for enabling the manual assembly of restocking packages based on data generated by the hardware of FIG. 3 or FIG. 4;

FIGS. 5A and 5B illustrate embodiments of an order assembly table;

The specification includes an appendix which includes eight pages (A1-A8) of flow charts illustrating the process flow for various functions of the carousel of the present invention, a one page chart (A9) illustrating a patient fill process performed by an automation device such as a robot, and a one page chart (A10) illustrating a cabinet fill process performed by an automation device such as a robot. The processes are implemented in the presently preferred embodiment by software, stored in any appropriate memory device, which is executed by a computer.

DETAILED DESCRIPTION OF THE INVENTION

Exemplary embodiments of the invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
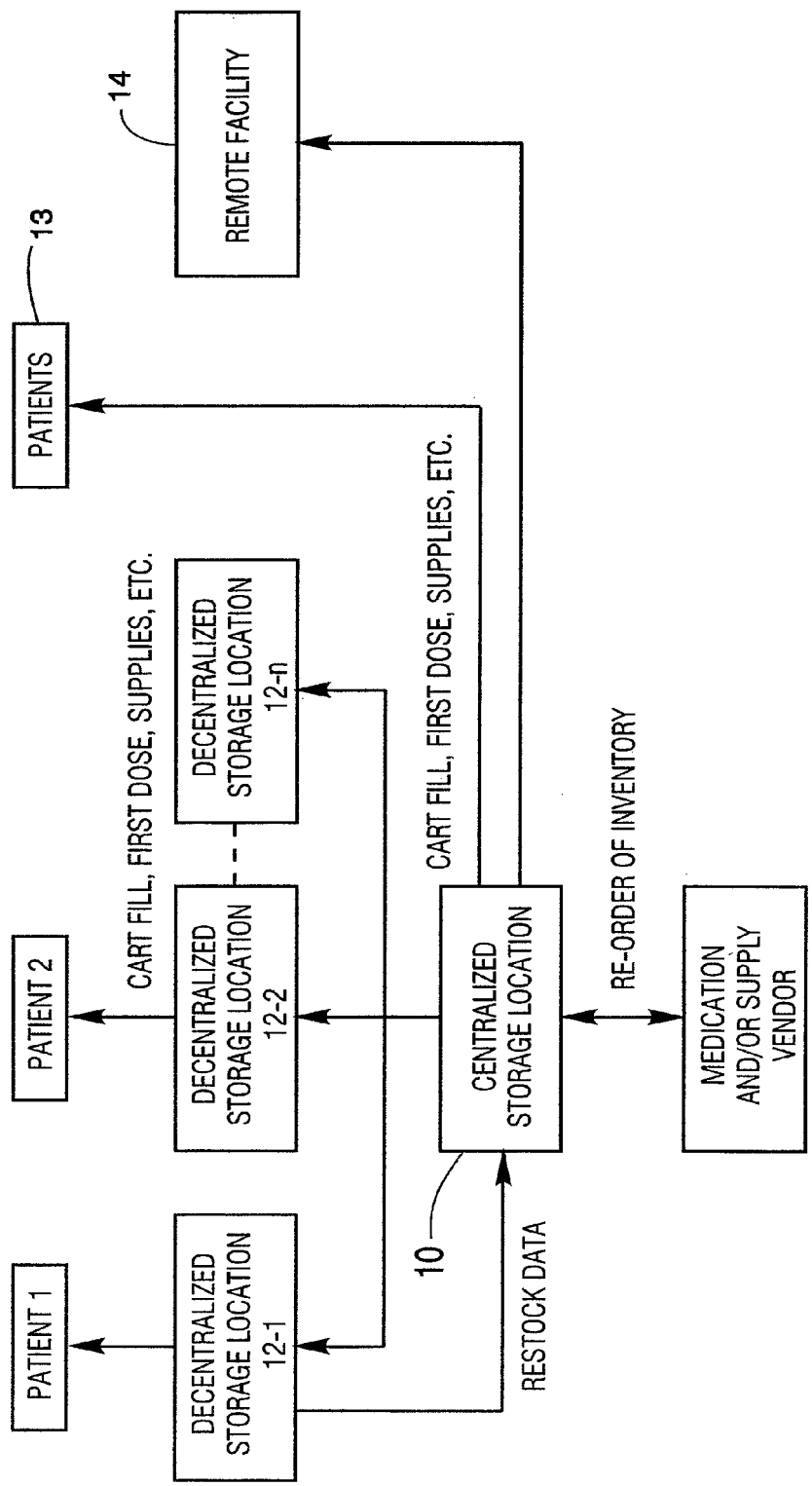
FIG. 1 is a diagram illustrating the relationship between a centralized storage location and, among other things, a plurality of storage locations.

FIG. 1 is a diagram illustrating the relationship between a centralized storage location 10 and various inventory destinations, including a plurality of decentralized storage locations 12-1, 12-2 through 12-n, patients 13, and a remote facility 14. Each of the decentralized storage locations 12-1 through 12-n is capable of dispensing items stored at the location. The items may include medications, controlled medical supplies, medical supplies or items of a nature consistent with the facility in which the system illustrated in FIG. 1 is located. Items may be dispensed directly from centralized storage location 10 to patients 13, or from the centralized storage location 10 to a remote facility 14. Data typically flows from the decentralized storage locations 12-1 through 12-n to the centralized storage location 10. In response to that data, items are typically moved from the central storage location 10 to the decentralized storage locations 12-1 through 12-n or to the remote facility 14 to restock such locations to either replenish dispensed items or to stock new items. Decentralized locations could include satellite pharmacies, computerized medication cabinets, stationary/mobile medication carts, nurse servers, remote hospital pharmacies, supply closets, supply cabinets, etc. Supplies can be reordered from distributors based on levels of stock in the centralized storage location 10.

Figure 2:
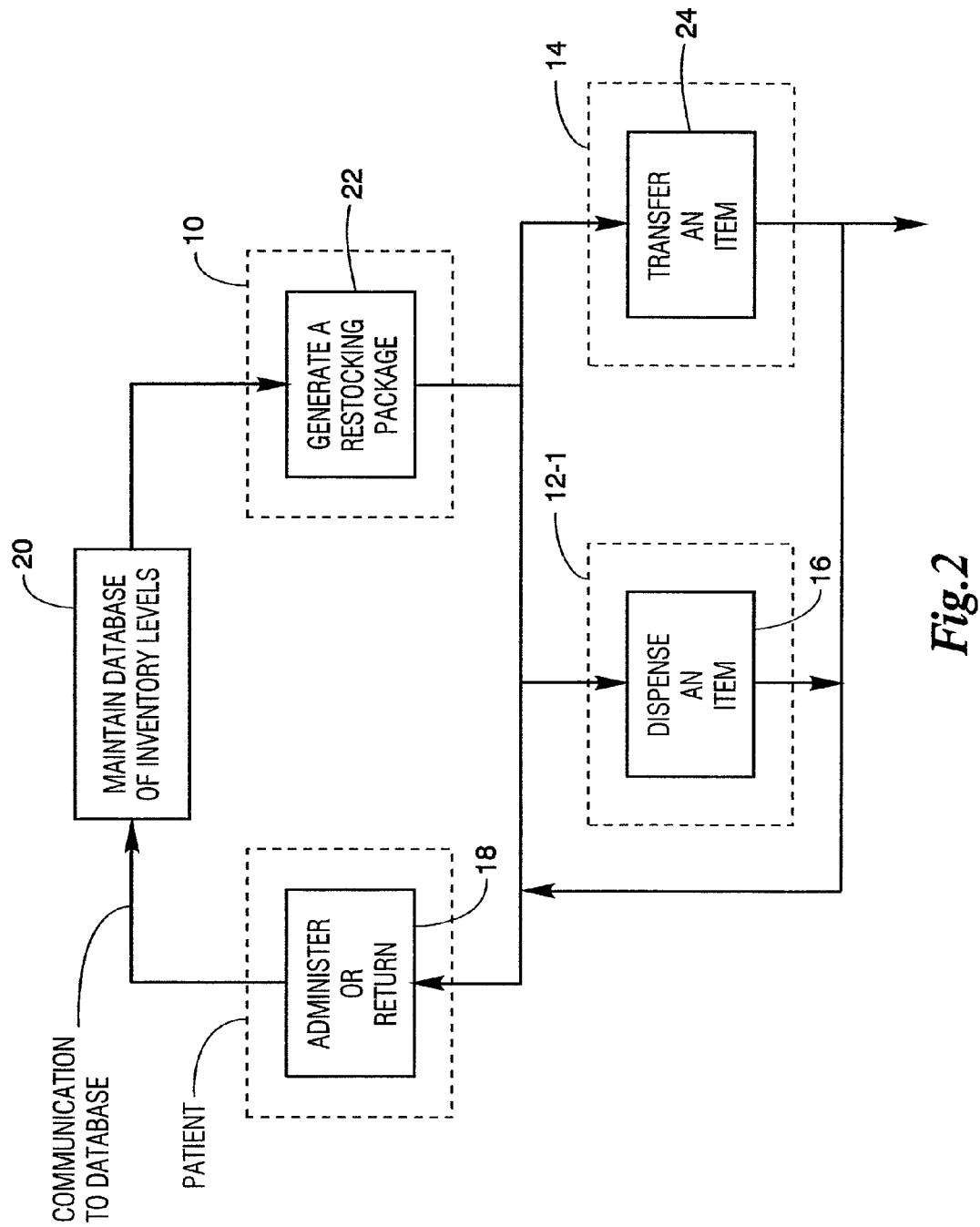
FIG. 2 is a diagram illustrating a process for distributing items and restocking of items based, at least in part, on records created during distribution.

FIG. 2 illustrates a process which may begin with a step of dispensing an item at step 16 from one of the decentralized storage locations 12-1 to a patient. A dispensing operation may occur in a variety of ways. In a medical facility, dispenses may be completed from medication orders or they may be completed from inventory lists, to name a few types of dispensing operations. Assuming a medication has been dispensed from decentralized storage location 12-1, the medication may either be administered to a patient or returned as shown by step 18. Medications may be returned for a variety of reasons such as the patient has checked out, been moved, or the patient's medication may have been changed. Medications may be returned to the decentralized storage location 12-1. Certain types of medications may simply be replaced in the decentralized storage location 12-1 so as to be used in another dispensing operation, or may need to be disposed of.

The administration of medications occurring at step 18 may be carried out through the use of a hand-held device such as an AcuScan-Rx™ device available from McKesson Automation, Inc., 700 Waterfront Drive, Pittsburgh, Pa. Such devices are wireless devices which communicate with a database to verify the administration of medications to patients. Such communications enable the maintenance of a database of inventory levels as shown by step 20. The database and associated computer system for maintaining the database of inventory levels may be located at the centralized storage location 10 or may be located remote therefrom. In either event, the computer system necessary for maintaining the database provides information which enables the centralized storage location 10 to perform step 22 of generating a restocking package. As will be described in greater detail below, the generation of the restocking package may be done completely automatically, manually, or through some combination of manual and automatic processes. The restocking package is used to restock the decentralized storage location 12-1.

Restocking packages may also be generated at centralized location 10 and delivered to the remote facility 14. From facility 14 an item may be transferred as shown by step 24. The transfer may be a dispensing step for a patient or a transfer to another location. Items may also be dispensed directly to the patient from the centralized location 10.

Figure 3:
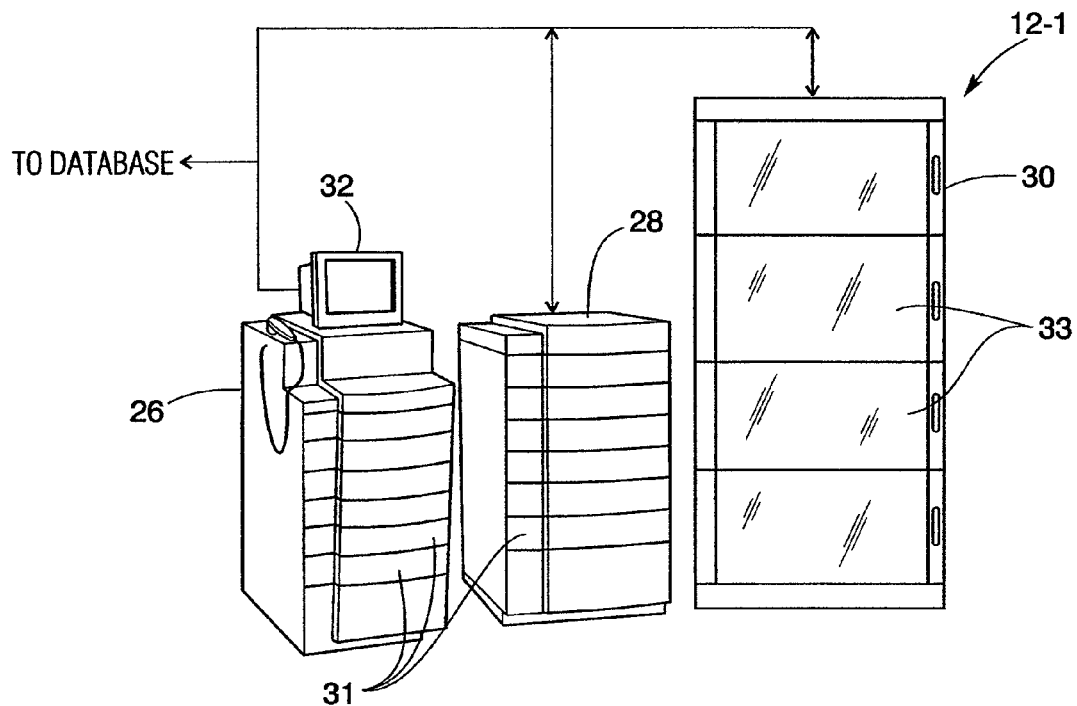
FIG. 3 is one example of hardware located at a decentralized location implementing a closed system for performing dispensing operations.

FIG. 3 illustrates one example of hardware which may be located at any of the decentralized locations 12-1 through 12-n. The hardware illustrated in FIG. 3 is comprised of an AcuDose-Rx™ cabinet 26, having a control computer 32, and an AcuDose-Rx™ auxiliary cabinet 28, available from McKesson Automation, Inc. A supply tower 30 is also illustrated. The control computer 32 controls the operation of the cabinet 26, auxiliary cabinet 28, and supply tower 30. The control computer 32 is also in communication with the central database.

To perform a dispensing operation a user logs onto the control computer 32. Based on the user's information, various drawers 31 in the cabinet 26 and the auxiliary cabinet 28, and various doors 33 on the supply tower 30 are unlocked. Thereafter, patient information and information regarding items to be dispensed is entered. The items to be dispensed may include medications or medical supplies. After the item to be dispensed has been removed, its removal is recorded at the control computer 32. The user may continue to dispense items for the identified patient, or patient information for another patient may be entered. Entry of information, including log-in, can be performed in a variety of ways, e.g., through entry with a keypad, barcode scanning, selecting items from a pick list, RFID, flash memory, magnetic strips, OCR, etc. Note that computerized medication cabinets like the AcuDose-Rx cabinet can also track medications or supplies that are not stored in the cabinets 26, 28 or tower 30. For example, the control computer 32 can track virtual inventories, i.e., medications stored outside the cabinets 26, 28 or tower 30. Examples include medications stored in a refrigerator whose inventory and transactions are recorded by the control computer 32. The reader will understand that the hardware illustrated in FIG. 3 is exemplary and is illustrated for purposes of demonstrating one type of hardware which may be located at the decentralized storage locations 12-1 through 12-n.

The hardware illustrated in FIG. 3 limits access to the items to be dispensed to those individuals who have properly logged on. Thus, the hardware illustrated in FIG. 3 is referred to as a closed system for performing dispensing operations because a dispensing operation cannot be performed unless the user is identified to, and recognized by, the control computer 32.

Figure 4:
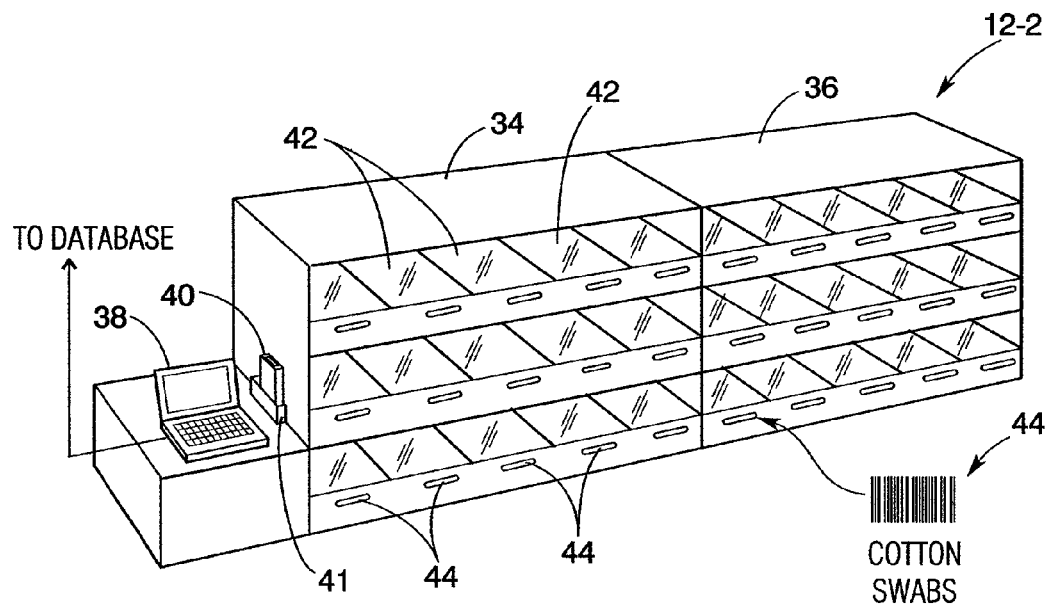
FIG. 4 is one example of hardware located at a decentralized location implementing an open system for performing dispensing operations.

FIG. 4 illustrates another example of hardware which may be located at any of the decentralized storage locations 12-1 through 12-n. The hardware is comprised of a first shelving unit 34 and a second shelving unit 36. An optional interface computer 38 may be provided, which is in communication with the database. If the interface computer is 38 is not provided, a handheld device 40 can be carried into the area to perform the inventory of the shelves. The handheld device 40 is taken back to the centralized storage location 10 where the information is downloaded in any appropriate manner. Alternatively, the hand-held device 40 could be a wireless device communicating over a wireless network link. Alternatively, and as shown in FIG. 4, the hand-held device 40 may be located in the area and have a docking cradle 41 in communication with the interface computer 38.

Each of the shelving units 34, 36 is comprised of a plurality of bins 42. Each of the bins carries indicia 44 which may be, for example, a barcode and/or a label identifying the contents of the bin. Additionally, items in the bins may have a bar code, label or other indicia directly on them or on their packaging. The bar code could be scanned, or other methods of inputting the data consistent with the type of indicia used, or push buttons or the like actuated, to perform a dispensing or other type of operation. In addition, the handheld device 40 could be used to generate an ad hoc order through its screen entry in the event that an item is not available to be scanned or otherwise have data pertinent thereto input. The number of shelving units 34, 36 and the configuration of the bins 42, depends upon the number and size of the items to be stocked. Because access to the bins 42 is not restricted, the hardware illustrated in FIG. 4 is referred to as an open system for performing dispensing operations. The reader will understand that the hardware illustrated in FIG. 4 is exemplary and is illustrated for purposes of demonstrating one type of hardware which may be located at the decentralized storage locations 12-1 through 12-n.

The hand-held device 40 may be a wireless scanning device such as a Symbol 7240 or Welch Allyn 7400. In one mode of operation, the operator may use the hand-held device 40 to scan the barcode indicia 44 for each bin for which a restock is desired. The operator will then input the order quantity on the hand-held device 40. When the hand-held device 40 is docked in its cradle 41, the data will be downloaded. The data will then be queued to be processed to generate a restocking package. Use of the hand-held device 40 eliminates the manual task of ordering items to be restocked, and reduces the potential for errors.

FIG. 5 illustrates one example of hardware located at the central location 10 for enabling the manual assembly of a restocking package based on data generated by the hardware illustrated in FIGS. 3 and 4. FIG. 5 illustrates a carousel 46 comprised of a plurality of bins 48 arranged in a plurality of rows 50. The rows 50 of bins 48 are connected to a drive track 52, which may be, for example, a pair of endless belts or chains. The rows 50 of bins 48 are connected to the drive track 52 through a swivel connection 54 which enables the rows 50 of bins 48 to maintain a horizontal position as the rows 50 are driven by the drive track 52. Each of the bins 48 carries indicia 55, which may be, for example, a barcode and/or a label indicating the contents of the bin, similar to indicia 44 in FIG. 4.

The drive track 52 is driven by, for example, an electric motor 56. The electric motor 56 may drive the drive track through one or more drive gears 58 in the case of a chain type of drive track or through a pulley in the case of a belt type of drive track. In addition to use of an electric motor 56, hydraulics or any other appropriate mechanism for driving the drive track 52 may be used. A sensor 60 may be provided to sense the position of the rows 50 of bins 48. Alternatively, a shaft encoder may be provided for motor 56 for keeping track of the degree of rotation of the motor's 56 shaft and, through knowledge of the gearing and the previous position of the rows 50, the position of the rows can be controlled. Use of the word "sensing" is intended to cover any of the various known method of sensing and/or calculating the position of the rows 50.

The carousel 46 is under the control of a workstation 62, which may be comprised of a personal computer in communication with the database. The workstation 62 receives information from the database regarding items, and quantities for each item, needed to replenish each of the decentralized storage locations 12-1 through 12-n or to fulfill patient dispenses. The workstation 62 processes the information and presents to the user through a screen 64 a series of operations referred to as "picks". The information displayed on the screen may include, for example, an identification of the decentralized storage location, an identification of a cabinet, tower, shelving unit, etc. at the decentralized location, an identification of the patient, the item and quantity to be picked. The workstation 62 also controls a printer 71 which can print barcode labels 72.

A label 72 with a barcode indicating the item (medication, supply, or kit) and the destination (cabinet, patient, etc.) will be printed from the printer 71. The user will scan that barcode with a scanner to activate the carousel picking process. The carousel dynamically evaluates the work queue of requests (patient dispenses, cabinet refills, on demand picks, stat, now, etc.) based on a configured set of priorities, set by the user. These priorities allow a medical facility to configure the order in which the different requests will be processed. Additionally, the facility may set up different priority ordering for different time periods in the day. For example, first doses may be disabled or prioritized lower during the hours of a cart fill. This work queue can also be paused at any time to perform an on-demand pick or restock. That allows user to pick an urgent item that may be in the queue.

To enable a pick to be performed, the workstation 62 activates motor 56 to bring the row 50 having the desired item into a pick position. In FIG. 5, the row 50' is illustrated in the pick position. When in the pick position, a plurality of indicia 66 are adjacent to each of the bins 48 in the row 50' in the pick position The indicia may include, for example, LEDs or an alphanumeric display. The location could also be indicated on an LCD Display or workstation 62. The workstation 62 may cause a number of LEDs equal to the quantity of items to be picked and adjacent to the bin 48 having the items to be picked to illuminate. Alternatively, an alphanumeric screen could be lit with the quantity of items to be picked from the adjacent bin 48. That is sometimes referred to as "pick-to-light" technology.

To finish the pick, a hand-held wireless device 68 is used to scan the bin label or item barcode 55. If the quantity that was picked from the device was not the full requested amount (because of an out of stock or expiration condition), the user can adjust the quantity picked and record a reason for the discrepancy before completing the pick. The barcode 72 that is printed at the beginning of the process (which initiates the picking) and the barcode on the bin or item that is scanned to complete the process are different formats to require the user to scan each of these barcodes (if the same information was encoded in each barcode, the user could scan one of the barcodes twice and would lose a critical validation to prevent picking of the incorrect item). An alternative method of indicating the completion of the pick could be to push a button or any other physical manifestation intended to represent the completion of the pick. The user then moves to the workstation 62 and initiates the next pick.

According to the present invention, when a pick is displayed on the workstation 62, the pick can be initiated either on the workstation 62 or via the hand-held device 68. Once the pick is processed, the hand-held device 68 may be used or a barcode on the centralized storage location may be scanned to indicate that the pick is complete and to initiate the next pick without having to travel to the workstation 62. In a large centralized storage location having numerous carousels 46 under the control of a single workstation 62, the ability to complete a pick and initiate the next pick using the hand-held device 68 eliminates travel time to and from the workstation.

To increase picking efficiency, a "place-to-light" system, described below in conjunction with FIGS. 5A and 5B, can be used which will allow multiple pick requests to be processed at one time. The system would print out multiple barcodes to begin processing of a batch of items. The user would locate these barcodes in identified locations, indicated by lights. The system would take the most efficient (shortest) path through the bins to pick items for the batch of requests. That allows more efficient movements of the carousel and, if several pick requests require the same item, the device can stop on that item's bin once and allow the picking for each item in the batch.

Figure 6:
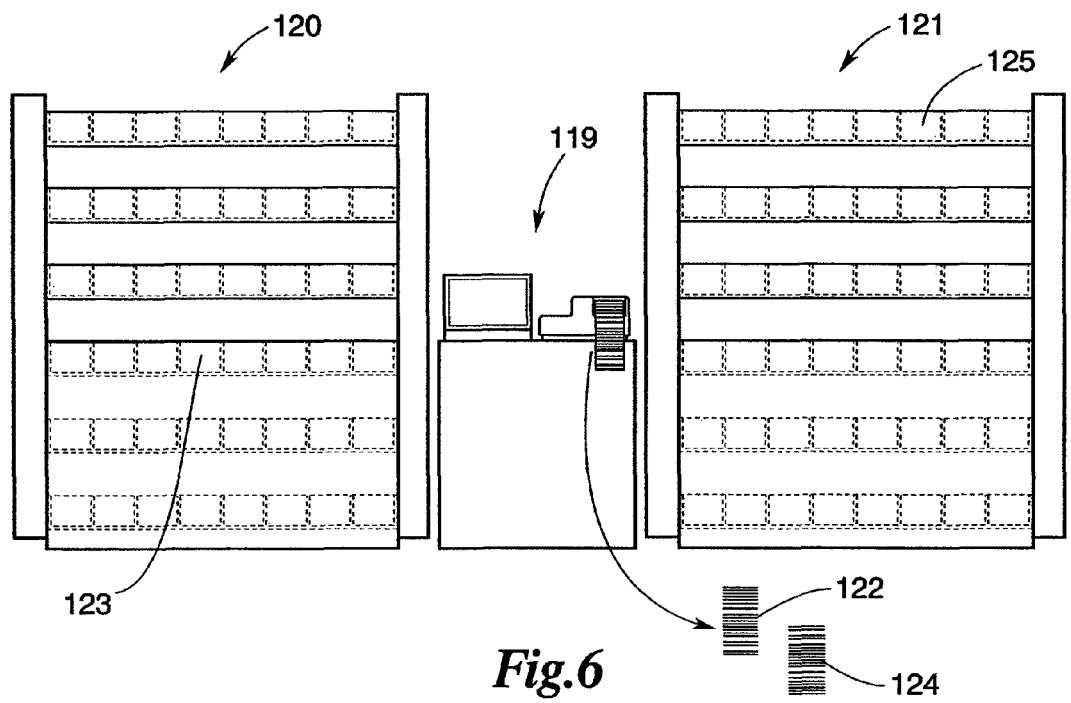
FIG. 6 illustrates two carousels and a workstation for implementing advanced queue processing.

Another way to increase efficiency is to implement advance queue processing for a medical facility that has multiple carousels. In FIG. 6, the carousel workstation 119 controls N number of carousels (two shown as 120 and 121, but there could be any number of carousels). The carousel system picks the highest priority item from the queue and prints a barcode label 122. The user scans the barcode and the appropriate carousel (based on current processing and the inventory stocked in the carousel) will move to the correct location. For example, carousel 120 will move row 123 into the pick position. The carousel system will automatically evaluate the queue and the carousels' status. If there is an idle carousel and the next item on the queue is located in that carousel, a label 124 will be printed and the carousel 121 will begin moving the rows to bring the correct row 125 into the pick position. This allows the carousel 121 to bring row 125 into place while the user is picking an item from row 123 from carousel 120.

Figure 7:
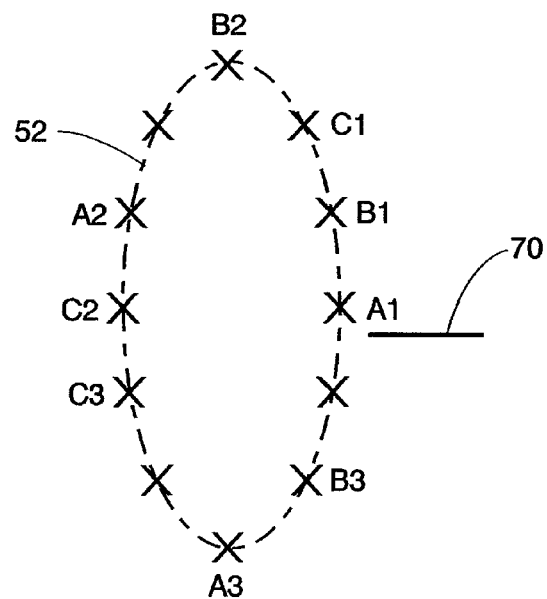
FIG. 7 is a diagram illustrating the order grouping feature of the present invention.

One of the features of the present invention is the carousel's 46 ability to be controlled in a manner so that a plurality of picks for more than one order can be processed. Referring to FIG. 7, a portion of the drive track 52 is schematically illustrated. Assume that the line 70 is representative of the pick position and each of the x's on the track 52 is representative of a row of bins. Assume further that three orders are being processed, one order each for patients (or decentralized storage locations) A, B and C and that three picks are needed for each. A-1 is representative of the first pick for A and it is seen that the row containing the first item to be picked for A is in the pick position 70. Moving counterclockwise around track 52, we see that the first pick B-1 for B is next, the first pick C-1 for C is next, followed by the second pick B-2 for B, etc. According to the prior art, picks for a patient/location would normally be queued and presented serially. Thus, after the pick A-1 is completed, the track 52 would be driven so that the pick A-2 could be performed, followed by the pick A-3. After the picks for A were completed, the row for pick A-3 would be in the pick position. Accordingly, it would be necessary to drive the row containing the pick B-1 into the pick position 70. Thereafter, the rows would be driven so that picks B-2 and B-3 could be performed. The three picks for C would then be serially performed.

According to the present invention, the picks for A, B and C may be integrated so as to minimize the time between picks. For example, referring to FIGS. 5A and 5B, two examples of an order assembly table 73 are illustrated. Each order assembly table has a plurality of locations 74, 75 and 76 which may be assigned to A, B, and C, respectively. Referring now to FIG. 6, the pick A-1 is completed and placed, through the use of light 74*a* indicating the location to be placed, in position 74. Thereafter, the pick B-1 is completed and placed in position 75 with the aid of light 75*b*, followed by the pick C-1, which is placed in 76 with the aid of light 76*c*. Then the pick B-2 is performed, which is placed in position 75, followed by the pick A-2, which is placed in position 74. The next two picks, C-2 and C-3, are placed in position 76, followed by pick A-3, which is placed in position 74, and pick B-3, which is placed in position 75, all with the aid of lights 74*a*, 75*b*, and 76*c*. Thus, by integrating picks, either on a patient basis, cabinet basis, shelving unit basis, or the like, the amount of travel experienced by the rows 50 of bins 48 is minimized, as is the time between picks. Information about the picks can be provided on the hand-held device 68, computer screen 64, and/or via the indicia 66, so that the user is provided with information regarding the item, quantity, and order to which the pick belongs.

Figure 8:
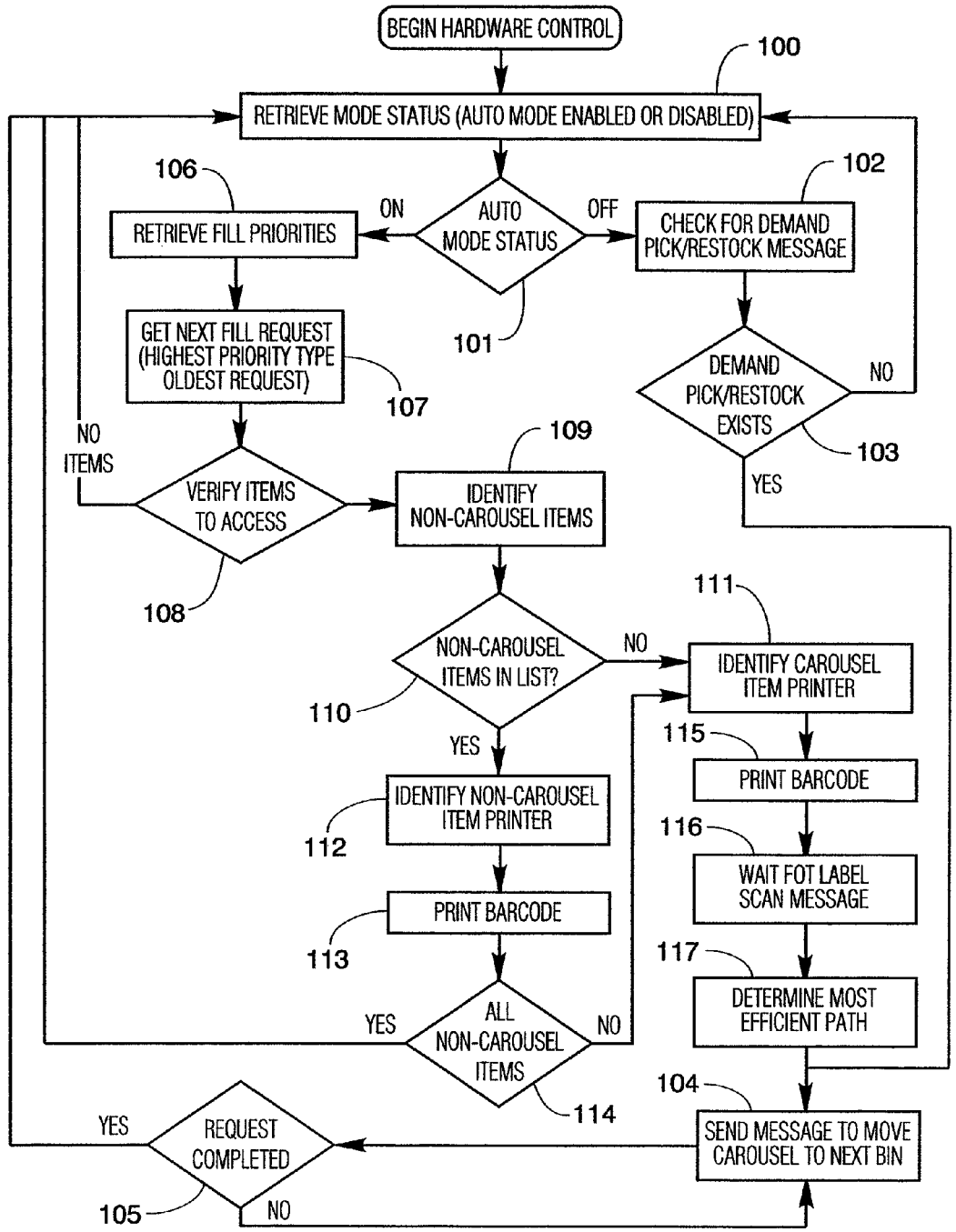
FIG. 8 is a flow chart illustrating the steps carried out by a processor controlling the carousel to process restocking orders in a batch mode.

FIG. 8 is flow chart illustrating the steps carried out by the workstation 62 for controlling the carousel 46. Beginning at step 100, a mode status is retrieved and queried at step 101. If the auto mode status is off, process flow continues with a check for "demand picks" at steps 102 and 103. If there are no demand picks, process flow returns to step 100. If there are demand picks, process flow proceeds to step 104 where a message is sent to move the carousel to the next bin. If the request is not complete as shown by step 105, another message is sent to move the carousel to the next bin, which continues until the request is complete, at which time process flow returns to step 100.

If at step 101 the auto mode is on, fill priorities are retrieved at step 106, and the next fill request is retrieved at step 107. A decision step 108 verifies that there are items to access. If there are no items to access, process flow returns to step 100.

If there are items to access, step 109 identifies if any are not in the carousel. Step 110 is a decision step that determines if there are any non-carousel items on the list and, if not, process flow proceeds with step 111 to identify the carousel printer 71. If there are non-carousel items on the list, the non-carousel item printer is identified at step 112, a barcode label is printed at step 113, and a decision step 114 determines if all items are non-carousel. If the answer at decision step 114 is "yes", process flow returns to step 100; if "no" process flow proceeds to step 111.

From step 111, process flow continues with step 115 in which a barcode label is printed. At step 116, the process pauses to wait for a label scan message indicating that the user has scanned the printed barcode label. At step 117 the most efficient path is determined. Process flow continues with step 104.

Carousels which may be modified to provide the functionality of the carousel 46 are available from a number of manufacturers such as White and Remstar. Exemplary hardware specifications are found in Table 1.

TABLE NO 1

Hardware Specifications
Remstar Model 180S-18-15 or equivalent

| | |
|---|---|
| Carrier Capacity (lbs.) | 485 |
| Total Unit Capacity (lbs.) | 13,448 |
| Number of Carriers | 18 |
| Number of Intermediate Shelves | 18 |
| Pitch (inches) | 15 |
| Height (feet) | 13'6" |
| Max Imbalance Load (lbs) | 1,540 |
| Depth of carrier (inches) | 15.0 |
| Max. Rotation Speed (inches/secs.) | 5.9 |
| Width of unit (inches) | 115.6 |
| Depth of Unit (inches) | 46.5 |
| Power Supply | 208/220 V 3 ~/60 Hz |
| Pick-to-Light Technology | |
| Remstar Controller T-88 | |
| 15 Amp service | |
| 480 Volts | |
| 1 posting board | |
| Beacon lights on shelf | |

Figure 9:
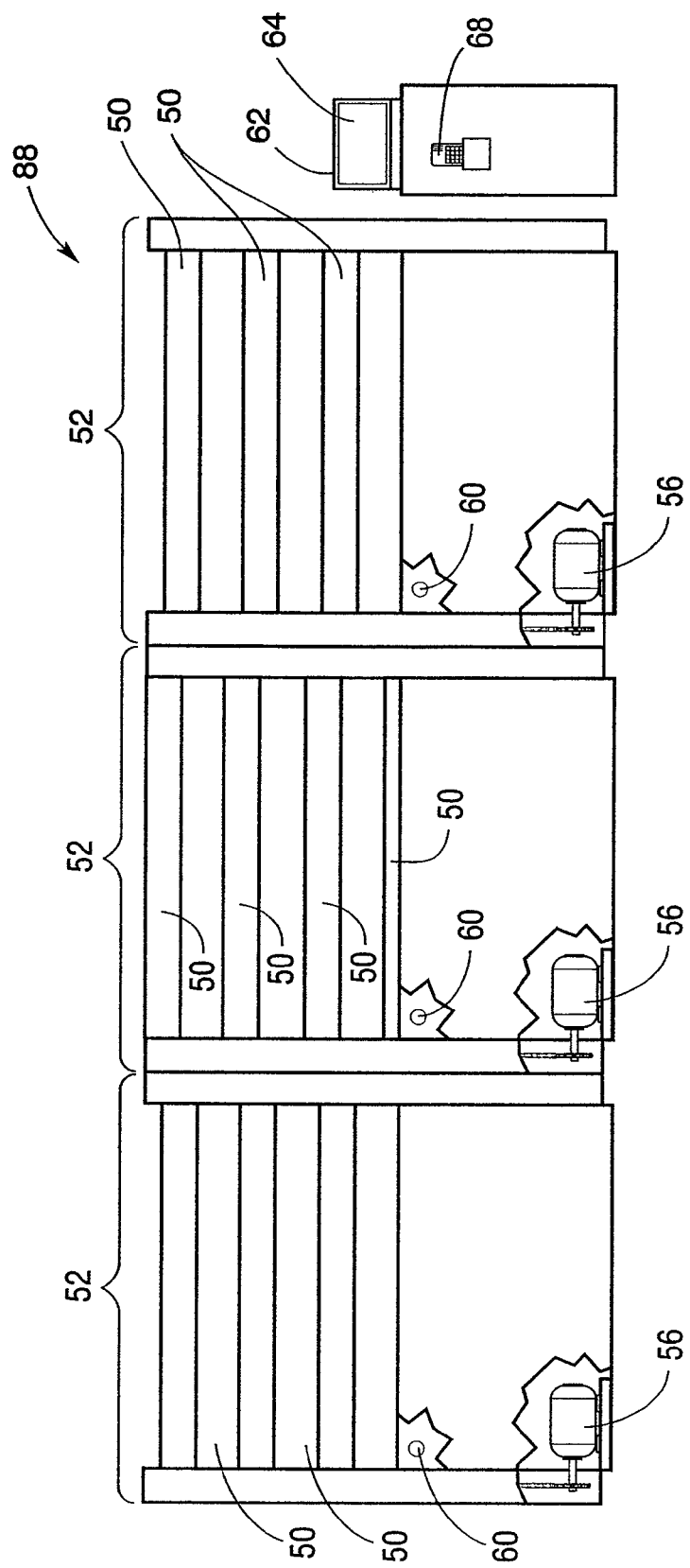
FIG. 9 is another example of hardware located at the central location for enabling the manual assembly of restocking packages based on data generated by the hardware of FIG. 3 or FIG. 4.

As seen from Table 1, carousels may easily be 10 feet or more in width. Because the carousel must be designed based on the heaviest item to be dispensed, the carousel may be considerably over-designed for many of the items to be carried. According to another aspect of the present invention, a carousel 88 may have a "slot-machine" design as shown in FIG. 9. The carousel 88 of FIG. 9 has a plurality of tracks 52, each having its own electric motor 56 and drive gears (not shown). Each of the drive tracks 52 has connected to it its own plurality of bins arranged in a plurality of rows 50. In that way, the carousel 88 may be designed in a number of discreet columns with one of the columns designed for dispensing heavier items, and the other columns designed for dispensing lighter items. The column dispensing the lighter items need not be engineered to carry the same amount of weight as the column designed to carry the heavier items, and therefore can be made more inexpensively. Additionally, because it is to dispense lighter items, a smaller motor may be used as well as different gearing. Another advantage of the "slot-machine" concept is the need for varying speeds in the automation. The fast moving items will be stored in the fast moving tracks and the heavier and bulkier items in a slower moving track. The multiple rotating columns could minimize wait times for the operator by indexing to the next pick location in the columns where the operator is not currently picking.

Although the present invention has been described in conjunction with a vertical carousel, the concepts of the present invention could be implemented using a horizontal type of carousel.

Other types of hardware which may be used at the centralized storage location 10 include a system of the type disclosed in U.S. Pat. No. 5,593,267 entitled "Automated System for Selecting and Delivering Packages from a Storage Area," U.S. Pat. No. 5,880,443 entitled "Automated System for Selecting Packages from a Cylindrical Storage Area," and U.S. patent application Ser. No. 09/480,819 entitled "An Automated Medication Dispensing System," all of which are hereby incorporated by reference. It is anticipated that the centralized location may be comprised of various types of hardware such as carousels illustrated in FIG. 5 and FIG. 9, and/or the hardware identified in the aforementioned patents and pending application. The centralized storage location may be completely automated, partially automated by having both a carousel and, for example, a computer-controlled robot, or completely manual by having one or more carousels. In that manner, a manual restocking system based on a carousel can be used side-by-side with an automated restocking system based on a robot.

Figure 10:
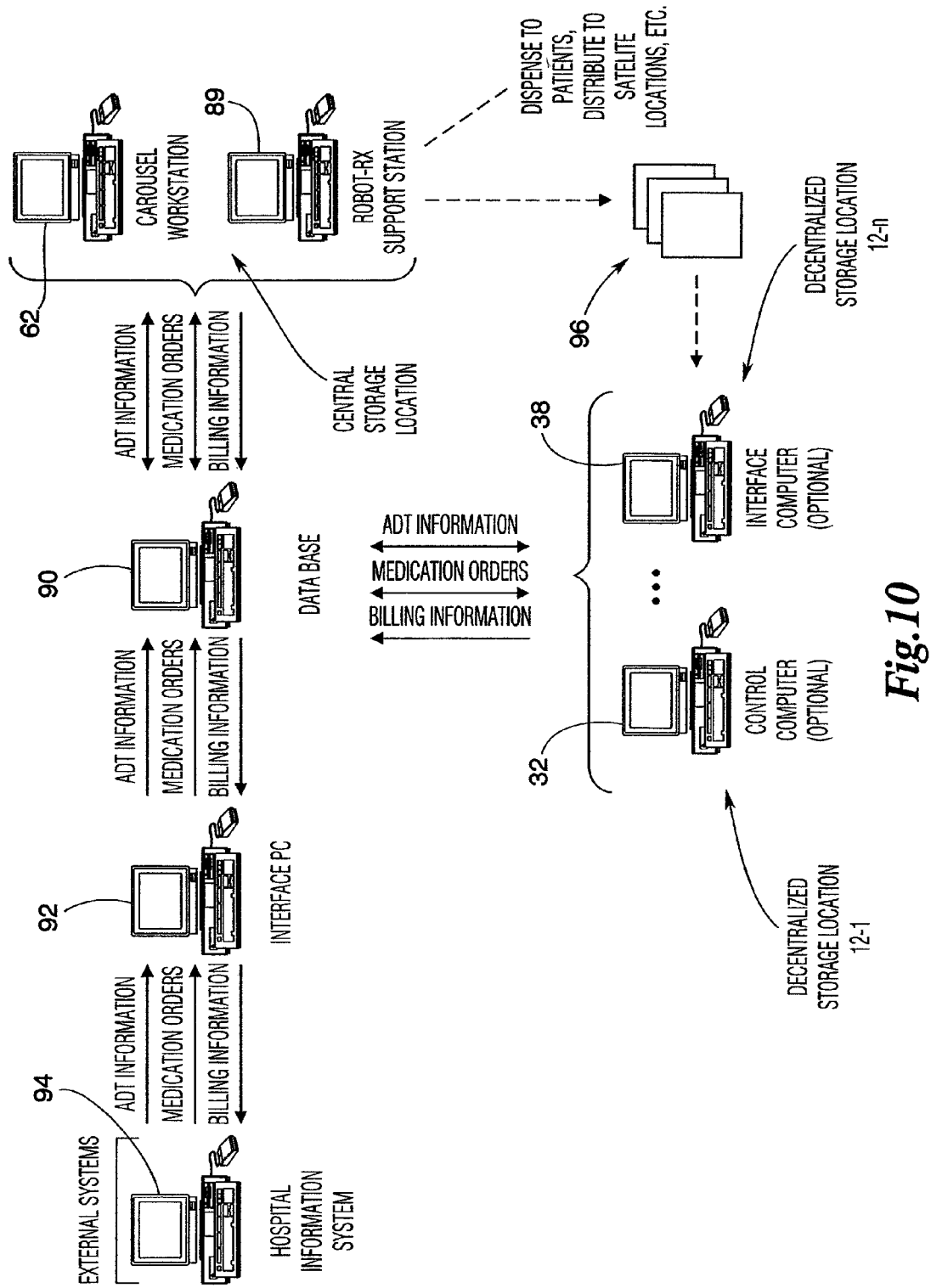
FIG. 10 is a diagram illustrating the flow of information between the computers used at various locations within a dispensing/restocking system.

FIG. 10 illustrates the computers used at various locations within a dispensing/restocking system of the type disclosed herein. As seen in FIG. 10, decentralized storage location 12-1 is where control computer 32 (if supplied) is located. Decentralized storage location 12-n is where interface computer 38 (if supplied) is located. The carousel work station 62 is located at the centralized storage location 10. The centralized storage location 10 may also have a Robot-Rx support station 89 which is used to control a robot.

A computer 90, which may be located at centralized storage location 10 or may be located elsewhere, maintains the database for the system. The computer 90 receives information from the decentralized storage locations 12-1 through 12-n and provides information to the carousel work station 62 and/or the Robot-Rx support station 89 to enable restocking packages 96 to be prepared. Additionally, dispenses to patients, distributions to satellite facilities, and the like may occur from centralized location 10. An interface PC 92 may be provided to enable external systems, such as a PC 94 on which a hospital information system resides, to communicate with the computer 90 on which the database is located. Completing the description of FIG. 10, as has been previously described, restocking packages 96 are prepared at the centralized storage location 10 and delivered to the decentralized storage locations 12-1 through 12-n.

The carousels 46, 88 of the present invention support cycle counts to verify inventory. The carousel system is semi-manual, so maintaining accurate inventory is very important to the operation of the system. To ensure accurate inventory levels, the carousel system supports various cycle count options which allow a user with the correct security privileges to periodically perform a physical count of the items in a bin. This process allows users to count controlled substances (based on DEA code) or other identified items (for example, high-cost or high-usage items) on one schedule (for example, daily or weekly) and then the remaining items on a different schedule (for example, monthly). In operation, the carousel will automatically move the shelves to the next bin that needs to be counted, the user will count the inventory and input the current inventory count into the workstation, and if a discrepancy exists, it will be logged with the user information and a reason. Once the count is completed, the carousel system will record the bin as counted with the current date and time and move to the next bin to be counted. The next bin will then be moved to and counted. The recently counted bins can be manually counted at any time, but will not show up in the automatic cycle count process until the next scheduled time. Such inventory counts help prevent out of stocks, help identify expirations, and provide better management of inventory.

Where centralized storage location 10 is used to restock decentralized locations 12-1 through 12-n having AcuDose-Rx™ cabinets, the restocking process may be initiated in an automated manner. The ability to track inventory levels on the AcuDose-Rx™ cabinets enables the database computer 90 to indicate when par levels are low and will trigger a flag for the restock to occur, as opposed to restock happening at periodic times or other methods not based on actual levels. Furthermore, the loop can be closed on the restocking process for AcuDose-Rx™ cabinets through the verification of the restocked orders at the cabinet. For example the carousel 46, 88 will process the restock orders for the AcuDose-Rx™ cabinet, and after the order is filled and delivered to the cabinet on the floor, the labels will be scanned at the cabinet to verify that the indicated amount on the restock report is actually loaded into the cabinet. This is especially useful for narcotics and other expensive or controlled medications. If the expected quantity to be restocked was not actually restocked at the cabinet, a discrepancy can be created and reported on or a notification can be displayed to the central location.

A system of the type illustrated in FIG. 1 implemented with the hardware of FIGS. 3, 4 and 5, and 9 may be provided with the following functionality.

Multiple and configurable fill times for batch fills. Each nursing unit can be configured with custom fill times, which will cause the carousel work station 62 and/or Robot-Rx™ support station 89 to fill orders only within the configured time period. Additionally, each nursing unit can be configured with more than one fill time to support centralized storage locations that do just-in-time or multiple fills per day.

Batch fills process off of delivery units, which are logical groupings of nursing units in the facility. This allows centralized storage locations to fill several nursing units at one time as part of a cart exchange (for example, all nursing units on the second floor).

Real-time admission, discharge and transfer (ADT) and order change processing during filling and a corresponding pre-delivery check. Any patient admission, discharge, or transfer or order discontinuing or changing a quantity will be processed during the fill processing. That prevents incorrect orders from being delivered and prevents patient medications from being delivered to the wrong room.

Track the delivery times for patients or decentralized locations that are filled by the carousel. That is important when filling patient orders, because knowing whether something made a cart fill or not would give the system the ability to know whether a first dose needs to be sent up to the patient to fulfill an order or whether it can be served by the cart exchange. Knowing when the delivery occurs lets you know whether an order change is caught by the pre-delivery check and is part of the delivery. It also gives the system the ability to get billing records correct for a patient.

Support for dose calculations to fill requests when a specific dose is not present. For example, one Tylenol™ 500 milligram table may be ordered, but may be filled by picking two 250 milligram tablets.

Support for medication kits. Orders for medication kits are for multiple items stored in the carousel. For example, a kit might consist of medication A, medication B, and the IV tubing necessary to deliver the medication. The system can associate one medication order to all three of these line items and dispense them and bill for them all as one item.

Different checking options exist to support different state regulations. Supported options include checking all orders, checking no orders, checking manually picked orders, and random checking of patients.

The carousel will implement two methods of restocking items that are low on inventory. One will be a static method, where the hospital configures a maximum and par level for each item in the carousel. Once the inventory falls below the par level, the item will be requested as a restock. The second method is to configure a maximum level, but to dynamically calculate the hospital's daily usage of an item based on historical data. This allows a moving average as item usage changes (changes in formulary or purchasing patterns, seasonal variations, etc.).

The events and transactions generated from the carousel and other automated systems will be moved to a separate long-term storage system. This system will record the dispense, inventory count, restock, and configuration (assignment and de-assignment) actions taken against the carousel, including, but not limited to, the following information: date and time, station, user, medication, and quantity. This data archiving system will allow users to periodically record these transactions to a recordable CD (CD-R). Because the carousel can store controlled substances, the recording of activity against these medications is required by law. Additionally, this storage system can provide long-term data analysis such as medication usage, processing efficiencies, and user actions.

Dispensing logic between pharmacy automation devices and unit-based cabinets. This logic helps prevent medications that could be dispensed from more than one system (pharmacy automation systems such as the ROBOT-Rx device or carousel, and unit based cabinets such as AcuDose-Rx cabinet) from being dispensed to a patient from multiple systems. A potential medication error is to, for example, allow a user to dispense a medication from a cabinet, and then have the same medication for the same order be delivered to the patient room from a cart fill or first dose fill from the pharmacy. The systems will evaluate whether the medication can be filled by a unit-based cabinet and/or a pharmacy automation product and decide, based on configurations, to which device to send the medication fill request. This functionality allows configuration on a unit or medication level, and allows configuration based on order types (PRN, scheduled, etc.) and DEA codes (controlled substances).

Configurable fill priorities which automatically send certain orders to a configured automation device based on priorities and status of the restocking devices. Fill priorities can include, but are not limited to, filling new medication orders, stat medication orders, decentralized inventories, etc.

Track the lot numbers for all medications or supplies stocked into the carousel. As a result, if a recall occurs, the system can know whether that lot number was ever in the carousel and to whom the medications or supply was dispensed.

Allow operators to process credits and returns of medications/supplies. Medications and supplies are often not used because a patient is discharged, orders are cancelled, or other reasons. As a result, it is important for the system to process these returns by crediting the patient's account for the returned medication/supply, returning it to stock, and then updating the carousel inventory.

The carousel will provide optimization processes which will identify, based on historical drug usage information, the optimal bin placement for the item. For example, the highest use items will be located on the same shelves to minimize travel distance between picks. Additionally, queue and pick processing will evaluate the optimal path to traverse. Inventory logic tracks the utilization rates of all medication in the carousel and generates reports which indicate which items might not be used frequently enough to take up space in the carousel as well as those items which receive a sufficient volume of orders to warrant being added to the carousel. These reports indicate high volume, non-automated items and low volume, automated items.

Items that could not be picked from the centralized storage device (because of an out of stock condition or because the item is not stored in the device) will be directed to a manual pick process. The manual pick process allows a pick report (exception list) to be displayed and printed, which displays a list of medications or supplies and the total quantity needed for the manual pick batch and displays a report for each patient identifying each item and the quantity required. The manual pick list displays patient information, including name, ID, location, and facility, along with order information such as the order description, route, frequency, dosage, and special instructions. Sites may configure to display the configured system drug name or the drug description passed with the order from the Pharmacy Information System. Additionally, the manual pick items may be directed to a label printer to generate a series of labels, one for each manual pick item.

Dispensing software which prints out a barcode (or other form of identification) to serve as a "license plate" for the dispensing package from the carousel. This license plate can be used to close the loop on the delivery of the package to its final destination, such as a computerized medication cabinet. As a result, if there is a diversion of medications or supplies and they don't make it to their intended destination, a discrepancy can be denoted, particularly if the ultimate delivery location is an AcuDose-Rx cabinet which is on the Connect-Rx platform with the carousel.

The carousel may send pick requests to an automated, controlled substance vault. Some controlled substances may not be able to be stocked in the carousel. However, the carousel control software could send a request to open the door to a controlled substance vault, like the narcotics vault, and lead the operator to pick a medication from this vault if it was required to complete a restock package or dispense.

The restocking packages 96 may take a variety of forms. The restocking packages 96 may also be patient specific or room specific. In one embodiment, the user delivers the patient or room specific restocking package to the decentralized storage location 12-1 through 12-n and is directed to load the medications into a patient/room specific area. In other embodiments, the restocking package is inserted into or connected into the unit's hardware. Dispenses are then made under the control of the control computer 32. Advantages of this approach include:

Development of a "nursing focused" medication administration dispensing system
    Dispensing patient specific medications
    Dispensing time specific medications
    Nursing unit specific
    Fixed or mobile
    Bar code driven In the various embodiments of the patient specific/room specific process medications are stocked in a robot system or a carousel system. A pharmacy information system (PIS) sends a fill list to the database computer 90, which sends instructions to either the carousel workstation 62 or the robot support station 89; medications are picked from the carousel or picked automatically by the robot, respectively. From that point on, the process is patient or room specific.

In a first embodiment of the patient specific/room specific process:

The picked medications are delivered into patient specific containers (envelope or bin) and may or may not be arranged in a time specific order.

The container is loaded onto a mobile cart which is identified for a particular decentralized storage location (statically or dynamically).

The mobile cart includes an on-board chip that carries the cart's ID.

Information about the medications currently stocked in the cart is also maintained by the on-board chip.

The cart is delivered to the decentralized location.

The cart is electronically connected to the control computer 32 (FIG. 3). Once connected, the control computer recognizes the mobile cart's ID.

Items are dispensed from the cart under the control of control computer 32. The mobile cart may include a visual indication to aid in the placement or retrieval of items.

As items are dispensed from the mobile cart, information maintained by the on-board chip is modified accordingly.

Bar coded envelope and/or medications may be scanned at the decentralized storage location for verification.

When replenishment becomes necessary, the mobile cart may be returned to the central pharmacy and connected to the carousel or Robot-Rx robot at which time the information on the chip may be accessed.

Once connected, the carousel or robot identifies the system and may automatically perform a refill for the mobile cart.

In a second embodiment of the patient specific/room specific process:

Picked medications are delivered into patient specific containers (envelope) and may or may not be arranged in a time specific order.

Figure 11:
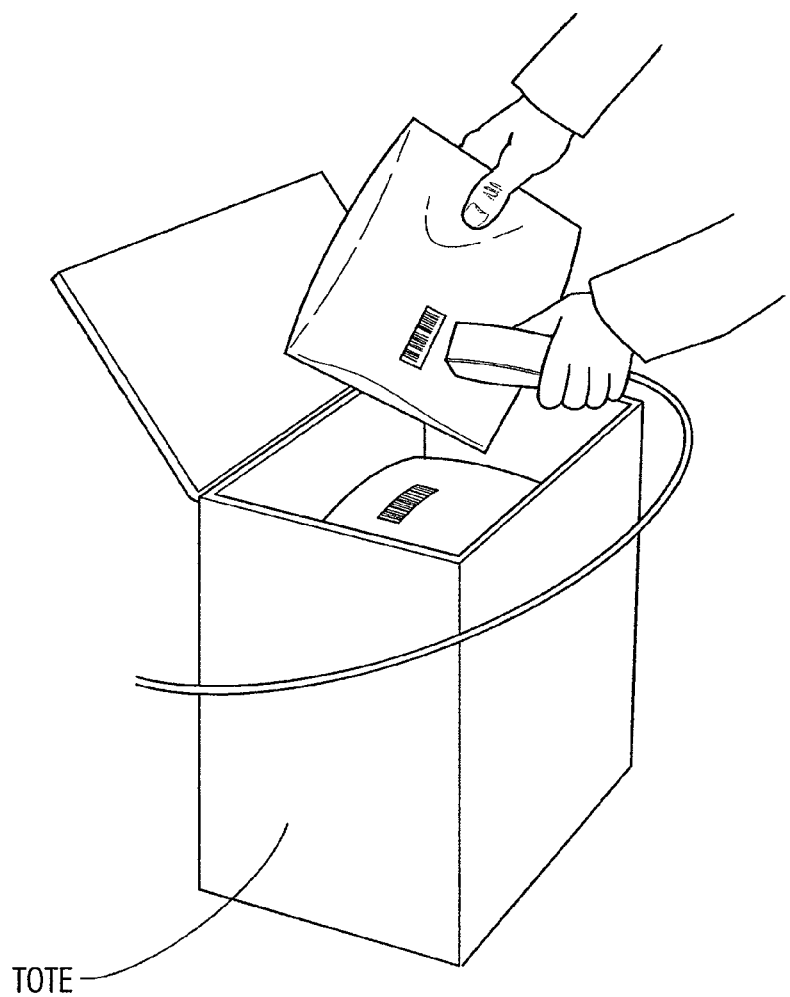
FIG. 11 illustrates a tote which may be used as a restocking package.
Figure 12:
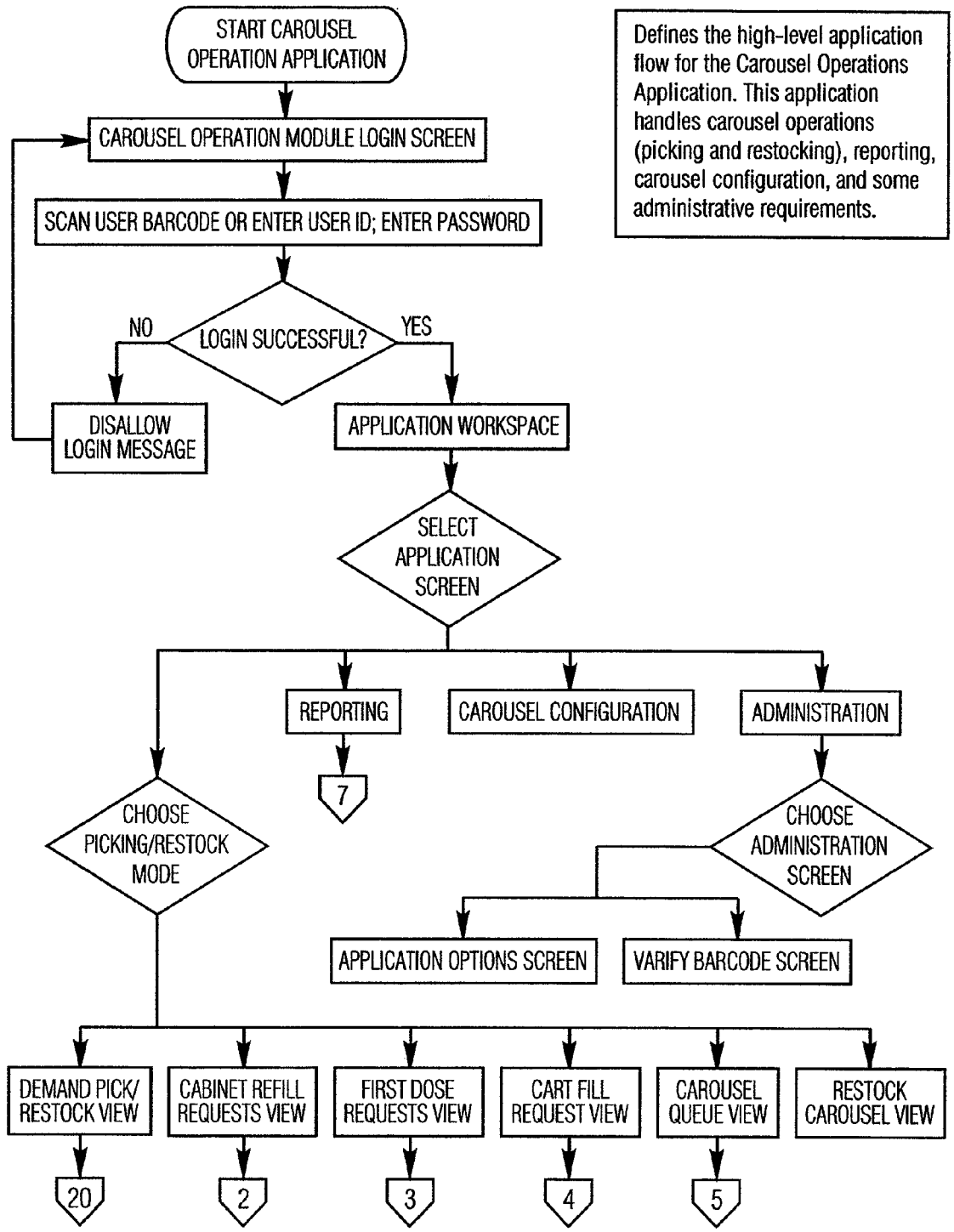
FIG. 12 is a flow chart illustrating a process flow for various functions of the carousel according to an embodiment of the present invention.
Figure 13:
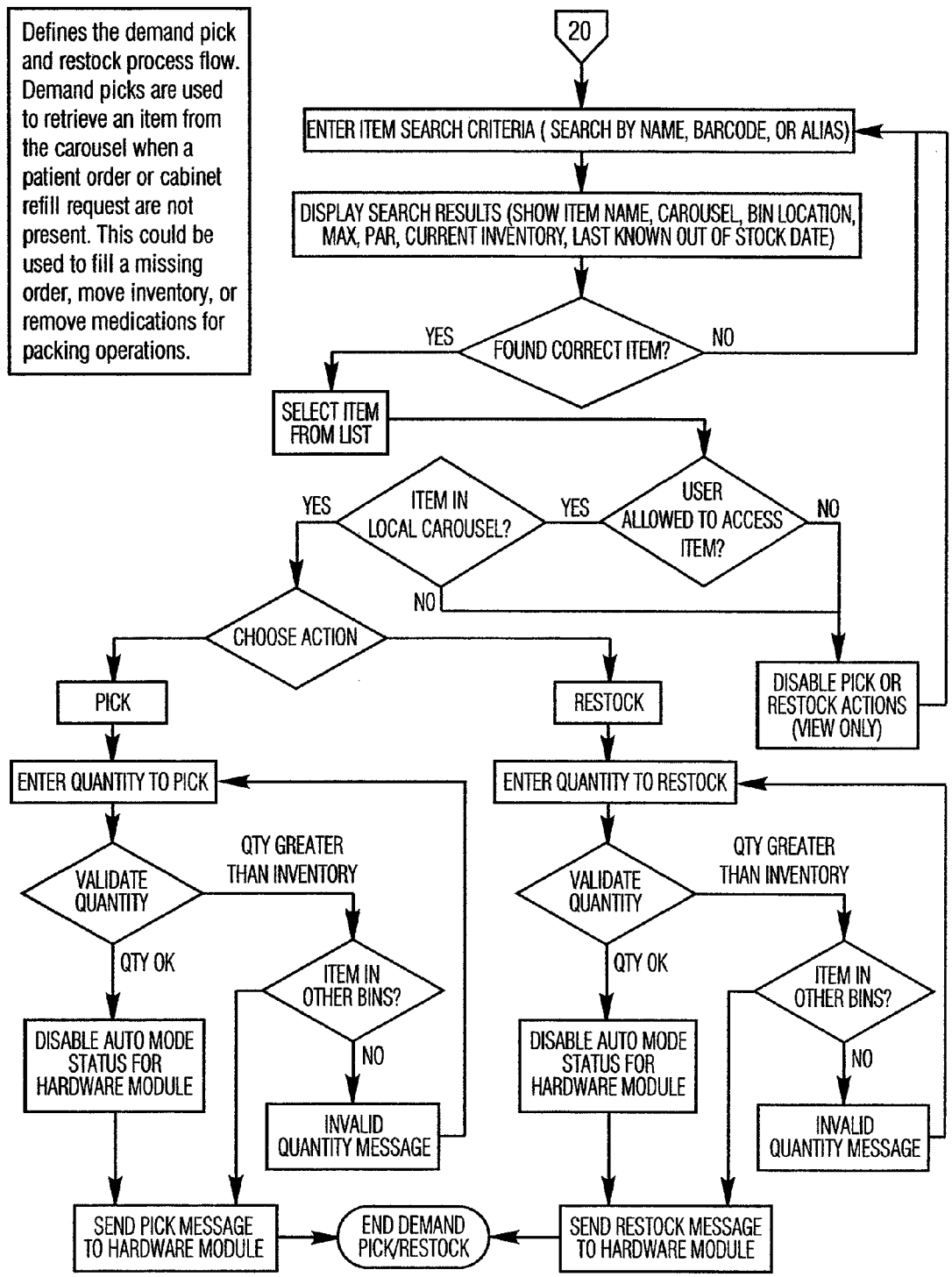
FIG. 13 is a flow chart illustrating a process flow for various functions of the carousel according to an embodiment of the present invention.
Figure 14:
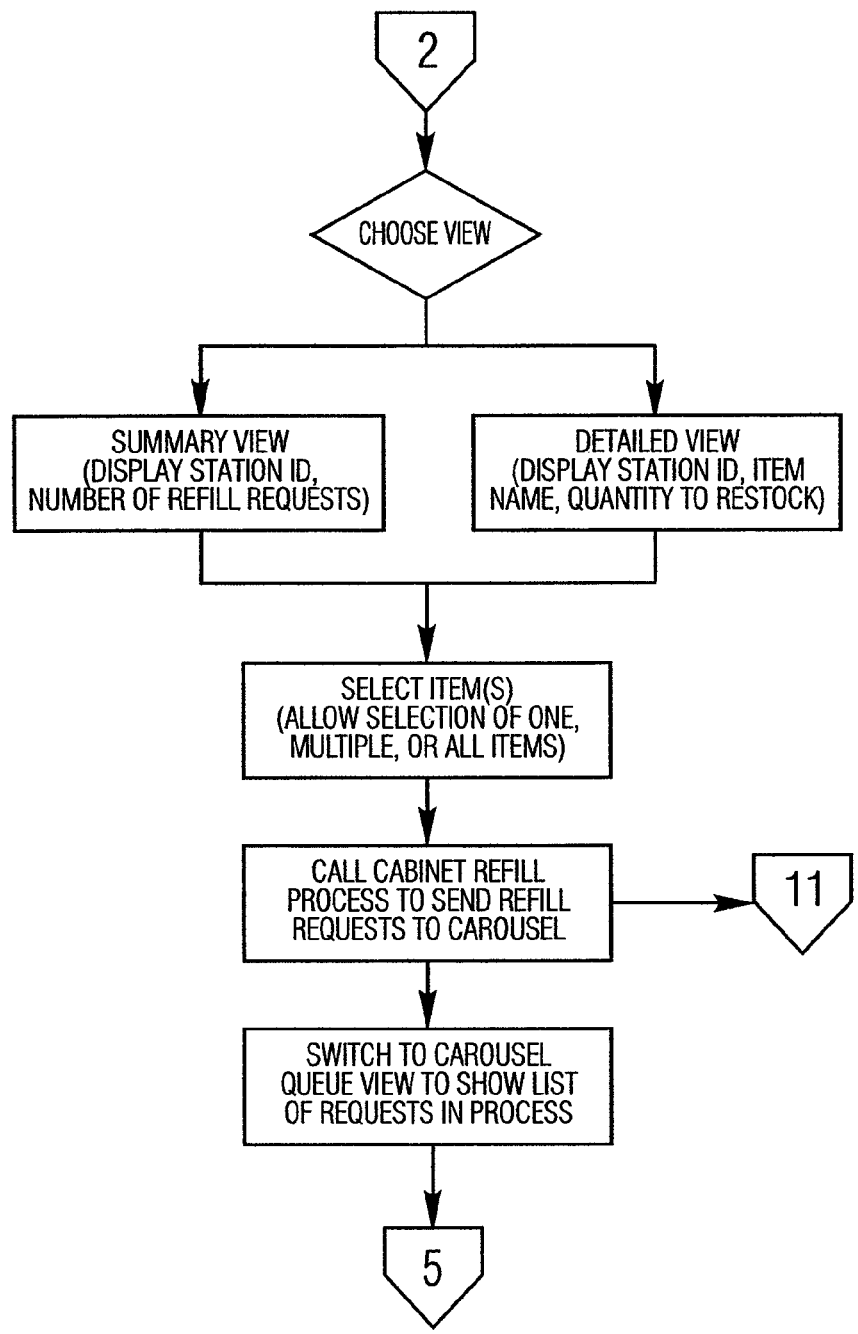
FIG. 14 is a flow chart illustrating a process flow for various functions of the carousel according to an embodiment of the present invention.
Figure 15:
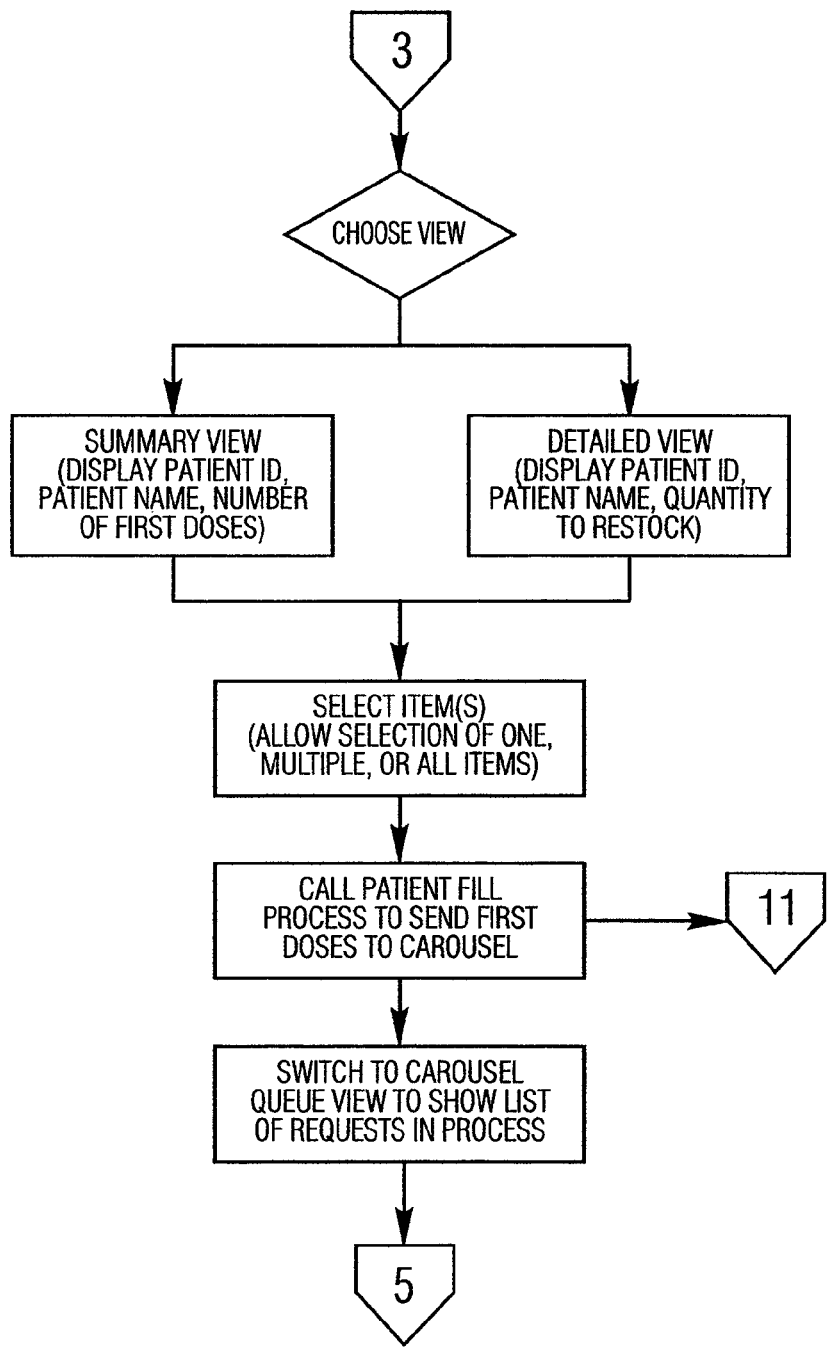
FIG. 15 is a flow chart illustrating a process flow for various functions of the carousel according to an embodiment of the present invention.
Figure 16:
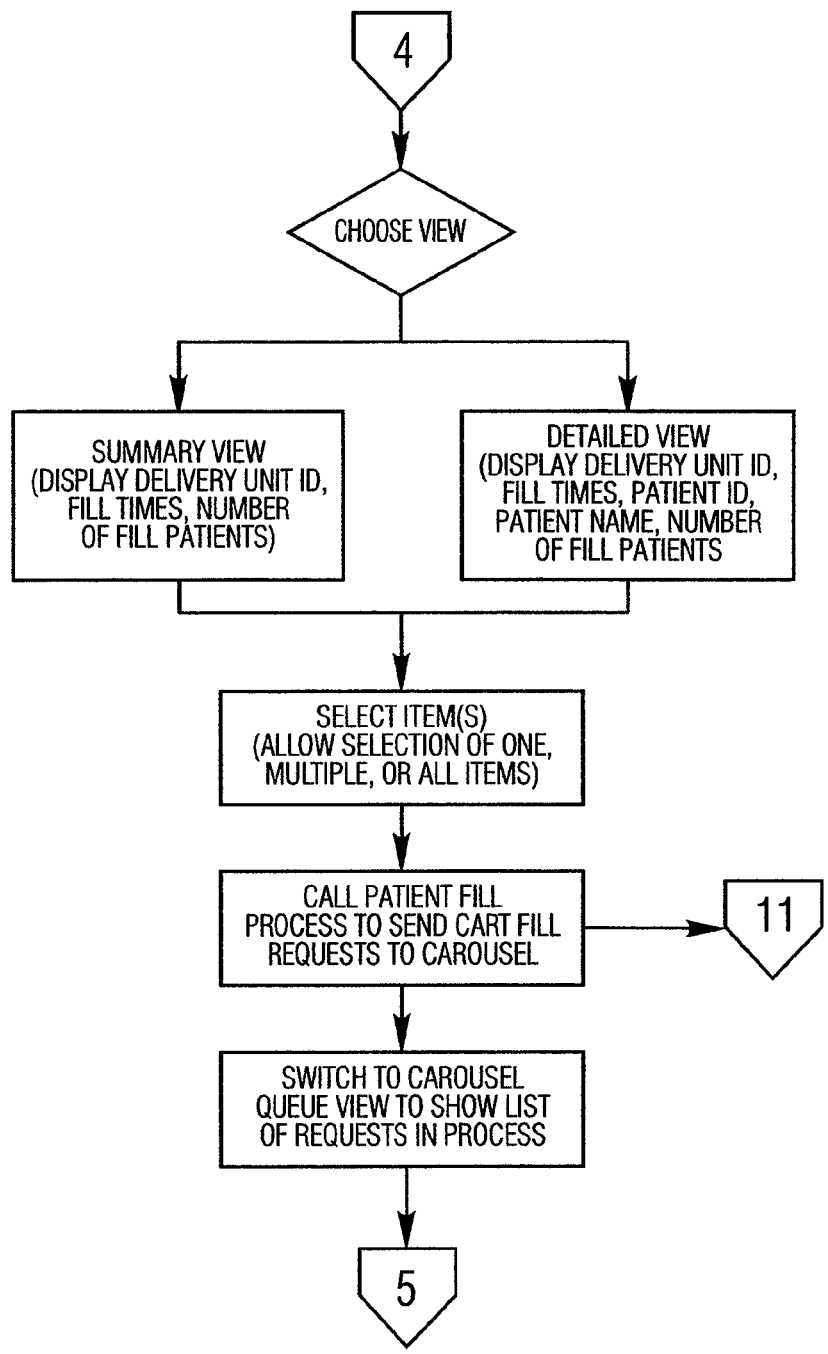
FIG. 16 is a flow chart illustrating a process flow for various functions of the carousel according to an embodiment of the present invention.
Figure 17:
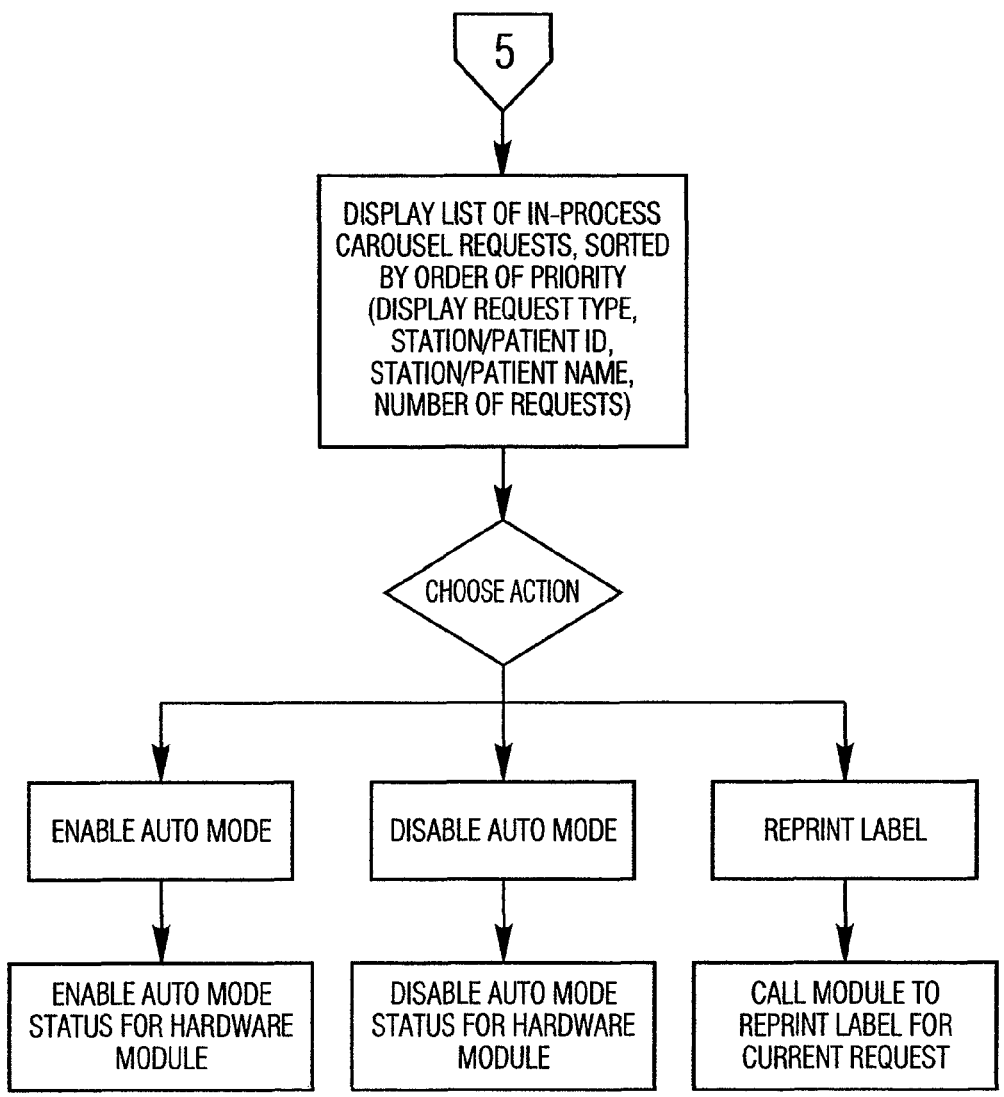
FIG. 17 is a flow chart illustrating a process flow for various functions of the carousel according to an embodiment of the present invention.
Figure 18:
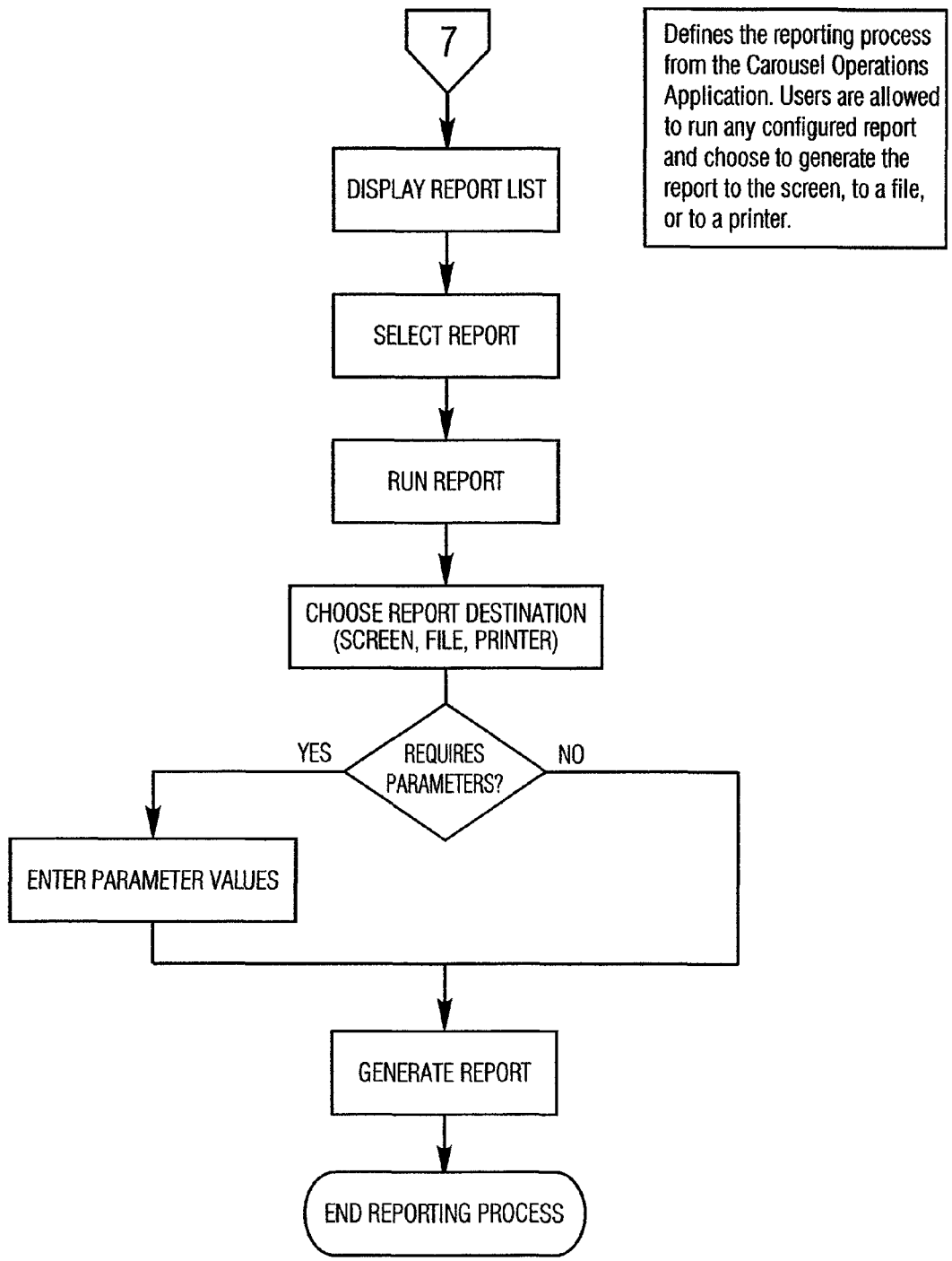
FIG. 18 is a flow chart illustrating a process flow for various functions of the carousel according to an embodiment of the present invention.
Figure 19:
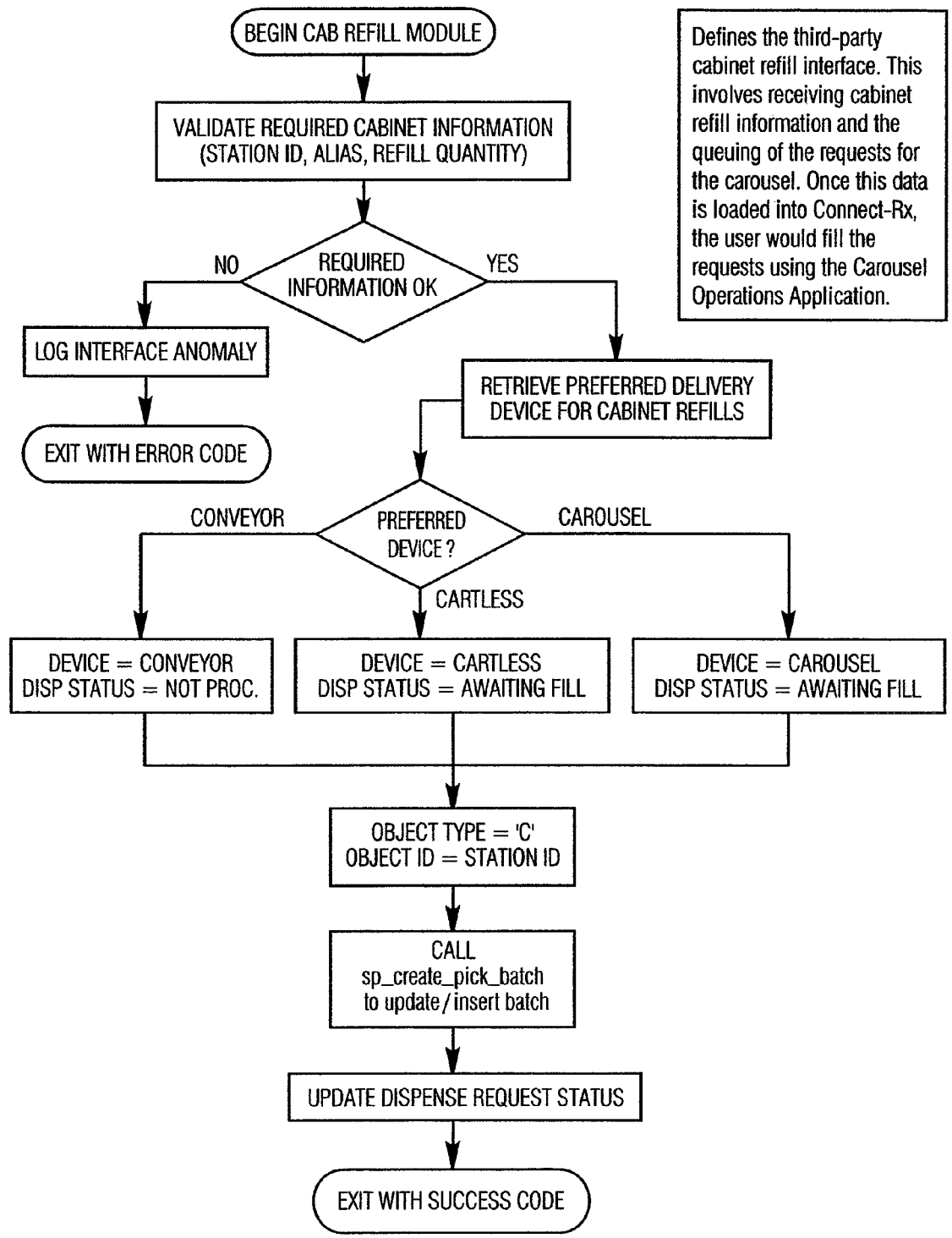
FIG. 19 is a flow chart illustrating a process flow for various functions of the carousel according to an embodiment of the present invention.
Figure 20:
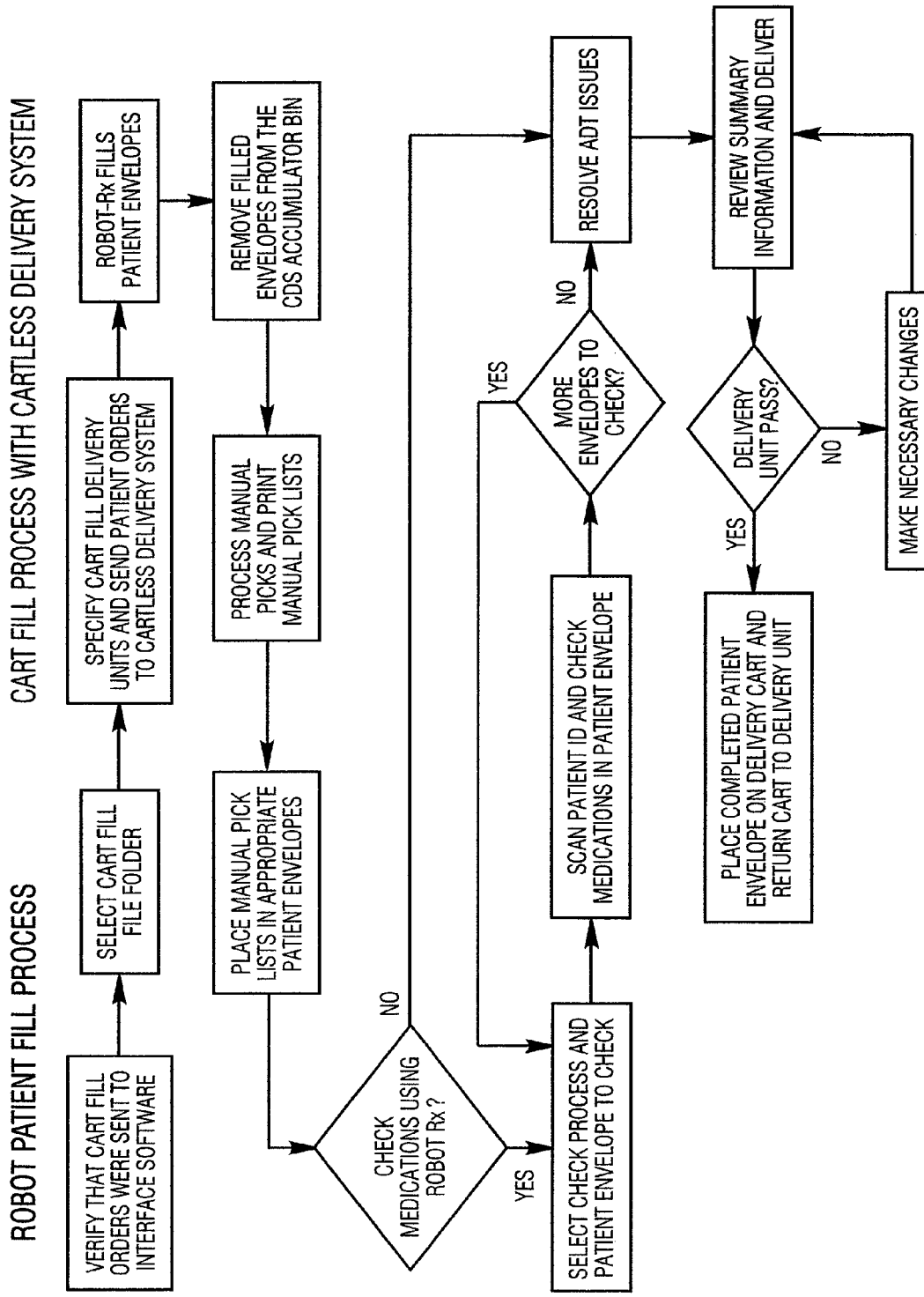
FIG. 20 is a chart illustrating a patient fill process performed by an automation device such as a robot according to an embodiment of the present invention.
Figure 21:
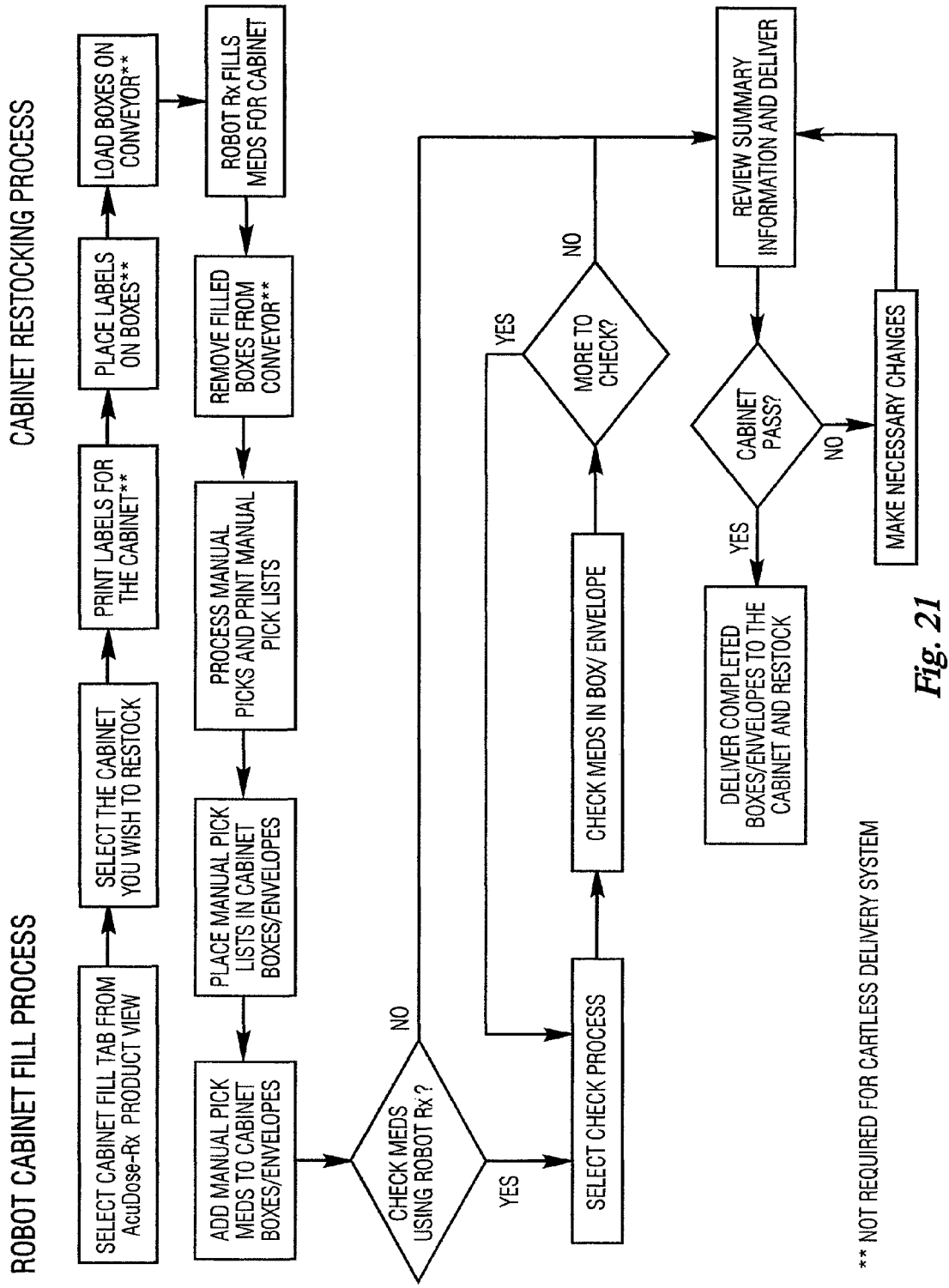
FIG. 21 is a chart illustrating a cabinet fill process performed by an automation device such as a robot according to an embodiment of the present invention.

The envelopes are loaded into a tote, see FIG. 11, which may include an on-board chip.

The tote is delivered to a decentralized location (with a tower) and identified at the control computer 32.

The tote is inserted into the tower or cabinet.

Items are dispensed from the tower under the control of the control computer 32.

Bar coded envelope and/or medications may be scanned at the decentralized storage location for verification.

In a third embodiment of the patient specific/room specific process: Picked items are delivered into a patient specific container, and may or may not be arranged in a time specific order.

Specific locations within the cabinet or auxiliary cabinet are designated as "patient specific pockets" and are lock-lidded.

The user scans the container at the decentralized storage location.

The control computer 32 recognizes the patient specific items and identifies the pocket into which the items are to be loaded.

Items are then dispensed from the cabinet or auxiliary cabinet under the control of computer 32.

Bar coded envelope and/or medications may be scanned at the decentralized storage location for verification.

While the present invention has been described in connection with exemplary embodiments thereof, those of ordinary skill in the art will recognize that many modifications and variations are possible. Accordingly, the scope of the present invention is intended to be limited only by the following claims and to any equivalents thereof.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method, comprising:
  filling an envelope with items in a centralized storage location;
  delivering said envelope to a dispensing device at a decentralized location; and
  inserting said envelope into a lock-lidded, patient specific location in said dispensing device, wherein inserting said envelope into a lock-lidded, patient specific location includes placing a tote containing patient specific envelopes into the dispensing device, wherein said tote contains a chip having information about the contents of said tote, wherein said chip is on-board said tote, and wherein said method additionally comprises dispensing from said tote and modifying the information in said chip in response to said dispensing.

2. The method of 1, wherein modifying the information in said chip includes modifying information relating to said patient specific envelopes.

3. The method of claim 1, wherein modifying the information in said chip includes modifying information pertaining to items contained in said patient specific envelopes.

4. The method of claim 1, further comprising scanning a barcode on the envelope to identify the patient specific location.

5. The method of claim 1, further comprising scanning a barcode on the envelope for updating records of the dispensing device.

6. The method of claim 1, further comprising returning the tote to the centralized storage location.

7. The method of claim 1, further comprising connecting the tote to an automation device and enabling the automation device to access the information on the chip.

8. The method of claim 1, further comprising tracking a delivery time of the envelope.

9. The method of claim 1, wherein the items include at least one of medications, controlled medical supplies, and items of a nature consistent with a facility in which the centralized or decentralized location is located.

10. The method of claim 1, wherein the decentralized location comprises one of satellite pharmacies, computerized medication cabinets, stationary/mobile medication carts, nurse servers, remote hospital pharmacies, supply closets, and supply cabinets.

11. The method of claim 1, wherein said dispensing from said tote is completed from medication orders or inventory lists.

12. The method of claim 1, wherein the centralized storage location is completely automated.

13. The method of claim 1, wherein the centralized storage location is completely manual.

14. The method of claim 13, wherein the centralized storage location includes one or more carousels.

15. The method of claim 1, wherein the centralized storage location is partially automated.

16. The method of claim 15, wherein the centralized storage location includes both a carousel and a computer-controlled robot.

17. The method of claim 1, wherein the items are filled in the envelope in a time specific order.

18. The method of claim 1, wherein the decentralized location is identified at a control computer.

19. The method of claim 18, wherein said dispensing from said tote occurs under control of the control computer.

20. The method of claim 1, further comprising scanning a barcode on the envelope for verification.

* * * * *